United States Patent [19]
Li

[11] Patent Number: 5,392,982
[45] Date of Patent: Feb. 28, 1995

[54] CERAMIC BONDING METHOD

[76] Inventor: Chou H. Li, 379 Elm Dr., Roslyn, N.Y. 11576

[21] Appl. No.: 123,877

[22] Filed: Sep. 20, 1993

Related U.S. Application Data

[63] Continuation-in-part of Ser. No. 804,287, Dec. 9, 1991, and Ser. No. 804,285, Dec. 9, 1991, Pat. No. 5,248,079, and Ser. No. 244,421, Sep. 16, 1988, Pat. No. 5,049,697, said Ser. No. 804,287, and Ser. No. 804,285, each is a continuation-in-part of Ser. No. 499,707, Mar. 27, 1990, Pat. No. 5,161,728, which is a continuation-in-part of Ser. No. 277,672, Dec. 14, 1988, abandoned, and Ser. No. 277,666, Nov. 29, 1988, Pat. No. 4,890,783, said Ser. No. 244,421, is a continuation-in-part of Ser. No. 277,672, Dec. 14, 1988.

[51] Int. Cl.⁶ .................... B23K 1/19; B23K 31/02
[52] U.S. Cl. .................... 228/124.5; 228/121
[58] Field of Search ............ 228/121, 122.1, 124.1, 228/248.5, 903, 124.5

[56] References Cited

U.S. PATENT DOCUMENTS

| | | | |
|---|---|---|---|
| 3,574,579 | 4/1971 | Clarke | 75/244 |
| 3,650,714 | 3/1972 | Farkas | 228/124.1 |
| 3,915,369 | 10/1975 | Schmidt-Brueken et al. | 228/198 |
| 3,949,263 | 4/1976 | Harper | 315/3.5 |
| 4,009,027 | 2/1977 | Naidich et al. | 228/122.1 |
| 4,239,502 | 12/1980 | Slack et al. | 51/295 |
| 4,396,677 | 8/1983 | Intrater et al. | 428/408 |
| 4,750,914 | 6/1988 | Chikaoka et al. | 51/293 |
| 4,776,862 | 10/1988 | Wiand | 228/122.1 |
| 4,899,922 | 2/1990 | Slutz et al. | 228/122.1 |
| 4,968,326 | 11/1990 | Wiand | 51/293 |
| 5,143,523 | 9/1992 | Matarrese | 51/293 |

FOREIGN PATENT DOCUMENTS 60-155600  8/1985  Japan ................... 228/124.5

Primary Examiner—Samuel M. Heinrich

[57] ABSTRACT

A method of coating and bonding a substrate with particles of a ceramic selected from the group consisting of diamond, carbon, graphite, and graphite or carbon-carbon composite, comprising: providing the substrate and at least one of the ceramic particles; selecting at least a carbide-forming substance consisting principally of an element which is other than Ni, Cr, and Co and is capable of forming a carbide to provide a coating material; applying said coating material onto at least one component of the substrate and the at least one ceramic particle; placing the at least one ceramic particle on the substrate; and heating the product of step (D) at a temperature sufficient to form a liquid-diffusion formed, carbide coating on the at least one ceramic particle. The ceramic particles are then coated with strong, adherent, substantially defect-free, and thermomechanically shock resistant metallized layers which are capable of practical uses over 630° C.

49 Claims, 2 Drawing Sheets

CERAMIC BONDING METHOD

REFERENCE TO RELATED APPLICATIONS

This is a continuation-in-part (CIP) of my pending U.S. application Ser. Nos. 07/804,287; 07/804,285; 07/244,421; respectively filed Dec. 9, 1991, Dec. 9, 1991, and Sep. 16, 1988, the later two now U.S. Pat. Nos. 5,248,079 and 5,049,697, respectively. The '287 and '285 applications are continuation-in-part's of my application Ser. No. 07/499,707, filed Mar. 27, 1990, now U.S. Pat. No. 5,161,728. The '707 and '421 applications are continuation-in-part's of my application Ser. No. 07/277,672, filed Dec. 14, 1988, now abandoned. The '707 application is a continuation-in-part of Ser. No. 07/277,666, filed Nov. 29, 1988, now U.S. Pat. No. 4,890,783. I hereby incorporate by reference all of the above-cited references.

BACKGROUND OF THE INVENTION

1. Field

This invention relates to ceramic coating methods, namely, methods for coating and bonding of ceramic on metal, of metal on ceramic, or of ceramic on ceramic; and more particularly relates to liquid-formed, ceramic coating and bonding methods with uniform ceramic metallizing compositions and specially graded, substantially defect-free bonded regions to produce reproducibly strong and thermomechanically shock-resistant coatings.

By ceramic I mean not only the usual ceramics such as alumina, zirconia, beryllia, mullite, cordierite, silicon carbide; but also quartz, intermetallics, diamond, boron, graphite, carbon, silicon, and various other carbides, nitrides, aluminides, or borides; glasses, machinable glasses, Corning's Vision glass; and the surface of many metals, particularly reactive metals such as aluminum, magnesium, chromium, silicon, titanium, or zirconium which always have oxides or other compounds of reactions of the metal with the environment.

2. Prior Art

Various methods have been developed to coat metal with, or to join metal to, ceramics. But none gives inexpensive, stable, strong, and temperature resistant products. Reliable ceramic coatings or joints are not commercially available worldwide at any cost.

Under a well-coordinated intensive effort on ceramic-metal bonding, Japan is the most successful country in the development and commercialization of products-involving metal-ceramic bonds. They already have successfully: 1) used a ceramic turbocharger (NGK, Nissan), 2) produced an all ceramic swirl chamber for diesel engines (Mazda, NGK), and 3) prototyped a ceramic turbomolecular pump (Mitsubuishi and Japan Atomic Energy Research Institute), according to Prof. T. Suga of the University of Tokyo in his 1989 review paper on the "Future Outlook in Japan" (copy enclosed). But the practical useful temperature of the best Japanese ceramic joints to special "matching" metal alloys is only 600° C. Further, the bond strength decreases rapidly with temperature, because the reaction products in their bonded regions become weak and brittle under thermal stresses. They consider the improvement of the thermomechanical shock resistance of the joints to be an urgent task. The European effort, mainly in Germany and France, has been even less successful. Germany failed to reach their goal after the first ten-year (1974–1983) program and its follow-up in 1983–1986. Their present program (1985–1994) merely emphasizes on achieving reproducible mechanical properties and component reliability. The US Department of Energy supports much of US ceramic joining R&D. It also had to renew annually the ceramic automotive program after 10-year, 50-million intensive work.

Many problems still exist with present ceramic metallizing and bonding methods. A serious problem is the instability and unreliability of even the best ceramic-metal bonds, as mentioned above. Another problem is the difficulty of achieving uniform metallized layers formed on the ceramic. Take, for example, the commonly used heavy metal processes, such as W—Yttria ($W-Y_2O_3$), W—Fe, or Mo—Mn. In these and many similar bonding methods, segregation of the mixed metal or other powders takes place due to their differing specific gravities, shapes, sizes, porosities, and surface smoothness. These segregation occur at all times: during the mixing of the powders, storing of the powder suspensions, application of the suspensions, settling of the suspended powders in the applied coatings of the suspensions, and drying of the applied coatings. Further, these segregations occur so fast as to be practically uncontrollable, as will be shown shortly.

In general, spherical, heavy, large, smooth, and dense particles settle first and early in the binder or suspension medium. Upon settling, these particles tend to roll or move sidewise or downward toward the corners or boundaries faster and further than odd-shaped, light, small, rough, and porous particles of otherwise identical characteristics.

Take the $W-Y_2O_3$ mixed powders in an organic binder of nitrocellulose in butyl carbitol acetate with specific gravities of 19.3, 4.5, and 0.98, respectively. Such a suspension, even if perfectly mixed up by shaking, stirring, roller-milling, or otherwise, will immediately tend to segregate. More specifically, the initial settling acceleration due to gravitational minus buoyancy forces on W powders is $980.6 \times (19.3 - 0.98)/19.3 = 930.8$ cm$\times$cm/sec, while that of $Y_2O_3$ powders is only 767.0 cm$\times$cm/sec.

In a mixing, storing, or carrying bottle 10 cm high and containing a perfectly mixed suspension of these metallizing powders, the time to completely settle out is only 147 ms (milliseconds) for W powders, if uniform acceleration is assumed. At the tip of a paint brush having a suspension drop 0.3 cm in diameter, the complete settling time of these same W powders is merely 25.4 ms, while on a horizontally painted or sprayed layer 0.1 cm thick, the same settling time is only 14.7 ms. In all these cases, the complete settling time for the $Y_2O_3$ powders is always the square root of $930.8/767.0 = 1.21$, or 21% longer.

Note in particular that the powder segregations with uniform accelerations may be completed within 147 to 14.7 ms. Such short times indicate that the $W-Y_2O_3$ powder segregations are beyond human controls. Painted or sprayed mixed powder layers are thus always not uniform.

In metallizing onto a horizontal ceramic surface to be metallized, most of the W powders immediately settles out. The first layers are therefore always very rich in W (melting point 3,410° C.), and correspondingly very poor in $Y_2O_3$. These first layers are too refractory for the preset metallizing temperature (up to about 1550° C.) so that the ceramic surfaces are not sufficiently metallized, or not at all. The last settling layers, on the other hand, are too rich in the fluxing $Y_2O_3$. Again, the ceramic surfaces are improperly metallized, with only a glassy layer being formed which is very weak in strength and thermal or thermal shock resistance.

Thus, common metallizing results on ceramics are often erratic and uncontrollable. The metallized surface may contain loose and unmetallized spots with high heavy refractory metal content, as well as non-wettable spots due to the high flux content. Additional brushings and nickel or copper platings do not solve the basic problem. The entire process is critical and involved, and yet nonuniform. The resultant ceramic-metal joints or ceramic coatings on metals are weak, costly, nonreproducible, and usually not vacuum-tight, or temperature-resistant.

Painting or spraying onto vertical or inclined surfaces results in vertical and additional lateral segregations and gradations, and gives added poor uniformity, reproducibility, and bonding strength.

While only the effect of gravitational density segregation has been considered in some detail, the other segregation variables such as powder shape, size, porosity, and surface roughness are also important.

A second important problem with common joining processes is the lack of control, or even understanding, of dynamic mismatches of temperatures, stresses, and strain profiles in the joint region, and their variations with time. Another aspect of this invention is therefore to describe such dynamic mismatch phenomena, and to specially tailor-grade the composition and/or physical property profiles of the joint region so that the maximum or critical transient mismatch stresses never exceed the local material strength at any point inside the joint region, at any time during the heating or cooling of such joints in processing or service.

A third problem results from our incomplete understanding of the required microstructural, chemical, and physical properties of the interfacial regions in the ceramic-metal joints.

Accordingly, an object of this invention is to provide improved ceramic-metal joints and joining methods;

A further object of this invention is to provide improved ceramic metallizing methods for these joints;

A broad object of this invention is to minimize gravitational segregations of the components in the metallizing methods during or prior to the joining;

Another broad object of the invention is to specially tailorgrade, both in and normal to the joining plane, the composition and/or property profiles in the joint regions to ensure that the maximum dynamic or transient stresses do not exceed the local material strengths at any point and time;

A further object of the invention is to provide a specially microengineered interfacial region of the optimum characteristics to achieve defect-free, tough, and very strong joints;

Another object of the invention is to flawlessly coated metals or ceramics with protective materials;

A yet another object of the invention is to provide substantially flawlessly coated reinforcements for the manufacture of tough, strong, thermochemically stable, and thermomechanically shock-resistant composites;

Further objects and advantages of my invention will appears as the specification proceeds.

SUMMARY OF THE INVENTION

To these ends, the method of the present invention method for coating a ceramic on metals or for making a structural joint between a metal and a ceramic for practical uses above 600° C. comprises uniformly metallizing the ceramic; and increasing the ratio of the ceramic material strength to the dynamic and static mismatch stresses due to differential thermal expansions so that these mismatch stresses do not exceed the ceramic material strength at any point and time thereby preventing bond failures.

DESCRIPTION OF THE DRAWINGS

The invention and its further objects and features will be more clearly understood from the following detailed description taken in conjunction with the drawings in which.

DESCRIPTION OF THE PREFERRED EMBODIMENTS

Figure 1:
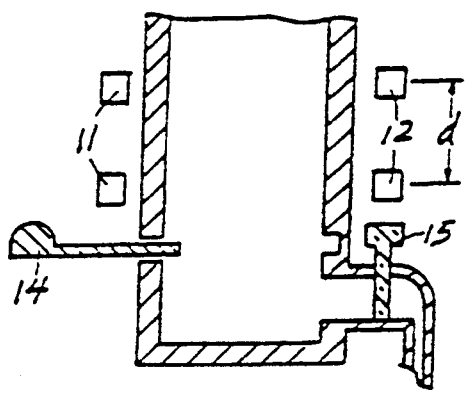
FIG. 1 shows a system for real-time monitoring of mixed settling powders.

It will be understood that the specific embodiments described herein are merely illustrative of the general principles of the invention and that various modifications are feasible without departing from the spirit and scope of the invention. That is, the invention is of general applicability for improving the quality of the ceramic-metal joints or joining methods, or coatings of ceramics on ceramics, or on metals. It is also evident that materials, structures, and methods other than those especially described can be used to practice the invention.

Stokes in 1851 first considered the resistance R which a fluid medium of density $d_m$ and viscosity n offers to the movement of a spherical particle of velocity v, diameter D and density $d_p$ suspended in it, and arrived at the equation $R = 3 \pi D v n$.

The small sphere settling in the fluid (i.e., gaseous or liquid) suspension medium is acted on by the force of gravity with gravitational constant g, $\pi D^3 d_p g/6$ acting downward; and by the buoyant force of the fluid, $\pi D^3 d_m g/6$, given by Archimedes' principle and acting upward. The resultant net gravitational force G is $\pi D^3 (d_p - d_m) g/6$ acting downward, producing a downward acceleration, a.

When the resistance R exactly equals this net gravitational force G, the acceleration reduces to zero; the final velocity, $v_f$, becomes constant. There then results:

$$3\pi D\, n\, v_f = \pi D^3 (d_p - d_m) g / 6$$

Hence, the final velocity is: $v_f = (d_p - d_m) g\, D_2 / 18\, n$, the equation of Stokes' law which has been shown to be widely valid.

For a given fluid density ($d_m$) at a specific temperature (viscosity n) and a given sphere (of density $d_p$ and mass M), the Stokes' equation gives a velocity constant:

$$v_c = v_f / D^2 = (d_p - d_m) g / 18 n$$

Also, the velocity at any time starting from rest, t, is:

$$v = (1 - \exp(-R\, t/M)) \times v_f$$

while the settling distance at time t is:

$$s_t = (t - (1 - \exp(-Rt/M)) \times M/R) \times G/R$$

The velocity equation shows that the exact $v_f$ is not reached until after infinitely long time when the exponential term in the equation turns to zero and then the velocity reduces to $v = v_f$, as it should.

With the Stokes' law, one can calculate the velocity constants, $v_c$ in 1/cm-sec, AND $v_s$, for the settling in water at 20° C. ($d_m = 1.0$ and $n = 0.010$) of various metal or oxide powders, with densities in g/cc in parentheses, as follows: W (19.35)100,000, $Y_2O_3$ (5.01) 21,900, Fe (7.87) 37,400, Mo (10.2) 50,100, Mn (7.2) 33,800, $WO_3$ (7.16) 33,600, $Fe_2O_3$ (5.24) 23,100, $MoO_3$ (4.692) 20,100, and $MnO_2$ (5.026) 21,900.

Thus, in the W—$Y_2O_3$ metallizing process, because the W powders are 3.9 (19.35/5.01) times heavier than $Y_2O_3$, the velocity constants c's of the two-components differ by a factor of 100,000/21,900 = 4.6 times. That is, for a given powder size D, the final constant settling velocity $v_f$ of W spheres is 4.6 times greater than that of $Y_2O_3$ spheres. As discussed above, this wide difference in velocities results in severe gravitational segregation and early depletion of W particles in the settling mixtures and, therefore, poor metallizing results.

It can also be seen that the powders in the mixed oxide processes, e.g., $WO_3$—$Fe_2O_3$, are much more uniform in densities, $d_p$, than mixed particles of the same metals, e.g., W—Fe. Thus, the $WO_3$—$Fe_2O_3$ process shows density and velocity constant ratios of 1.366 and 1.455, vs 2.459 and 2.674, respectively, for the W—Fe process.

Similarly, in the Mo-Mn process, replacing the metal powders by their respective oxides reduces the differences in the ratios of velocity constants, $v_c$, and final velocities, $v_f$, from 48.2% to only 9.0% and 19.2% to 4.2%, respectively. In addition, the metal particles, i.e., W, Fe, Mo, and Mn when reduced during metallizing from their respective oxides are smaller than the initial oxide powders. These smaller-sizes further promote homogenizations and metallizing results.

If we select and mix and $Fe_2O_3$ and $WO_3$ spherical powders in the size (diameter D) ratio of the square root of (33,600/23,100 = 1.455), i.e., 1.206, the final settling velocities of both these size-ratioed powders will be exactly the same. That is, by simply making the $Fe_2O_3$ powders 20.6% larger than the $WO_3$ powders, the mixed particles will finally settle in water at 20 C. at exactly the same velocity. This condition leads to metallizing uniformity due to the uniform composition of the finally deposited layers.

The final settling velocities of the two mixed powders, $v_s$'s, however, come only after some settling time, $t_s$, when a specific amount, Q, of the mixed powders has already settled out at differing velocities. From this settling time, $t_s$, for the specific combination of component powders, the settled amount Q and material use efficiency can be computed from the materials remaining after the settling time, $t_s$. The materials already settled before $t_s$ is the presettled distances, $s_t$, multiplied by the initial material densities. But the already settled materials are not lost, since they can be recirculated and reused in subsequent metallizing runs.

In this way, gravitational segregations between, for example, co-settling W and Fe, Mo and Mn, $WO_3$ and $Fe_2O_3$, or $MoO_3$ and $MnO_2$ powders, are minimized. Naturally, the smaller the percentage of velocity or useful powder size differences, $\Delta v$ and $\Delta D$, respectively, the lower the material use efficiency on a particular mixed-powder combination. An engineering compromise must, therefore, be struck.

The fluid suspension medium may be either a gaseous or liquid medium. The liquid may be water, alcohol, other inorganic or organic liquids of fairly constant viscosity at room temperature. A varying viscosity liquid may also be used, for example, a polymerizing organic substance containing a polymer and a hardener, a nitrocellulose in an evaporating solvent such as butyl carbitol acetate, or Duco cement diluted with rapidly evaporating acetone, to achieve rapidly increasing viscosity, n. The velocity constant of the settling powders is, as shown above, inversely proportional to this viscosity. In all cases, the starting time for achieving nearly equal settling velocities is shortened by the increasing viscosity due to polymerization or solvent evaporation. With increasing viscosities, the absolute difference in centimeters per second between the settling velocities of the two mixed powders of differing densities then become less, and nearly equal-settling conditions of powders are more easily achieved. The real-time monitoring system to be described in FIG. 1 is also useful, but the nearly equally settling mixed powders must be quickly used before much further polymerization or evaporation takes place.

Apparently, the above technique for minimizing gravitational segregation through minimized settling differences can be used to handle more than two types of powders of differing densities. Because the ceramic metallization reactions are diffusion controlled, the chemical composition of resultant metallized layer, though substantially uniform in any plane parallel to the bonding plane, still depends on the (diffusion) distance from the metal substrate surface.

In practice, we specify that the two settling velocities of the mixed particles are within a certain prespecified percentage, e.g., 20 or 10%, of each other. Still, gravitational segregations are minimized.

By repeated experimentation and computer iterations or simulation, the best mixed-powder metallizing process for optimal combined metallizing uniformity and material use efficiency can be systematically determined. Based on these principles, method and equipment can be developed for controlling the turn-on time for starting to deposit the mixed powder at nearly equal final settling velocity, $v_f$, into metallizing layers with the size-ratioed powders.

In FIG. 1 shows a system for real-time monitoring of the settling particles employed to determine the starting time for collecting the residual or still unsettled mixed particles to be used for metallization. This system has a vertical settling cylinder 10. Near the bottom of the cylinder 10, two pairs of light emitters 11 and detectors 12 are located at two different heights with emitters on one side and detectors on the opposite side of the vertical cylinder 10, to sense the settling particles. The times for the particles to pass the top or bottom emitter/detector pair determine the particle size or type being monitored, while the times for the particles to transverse through the vertical distance d between the heights give their velocities. When the settling velocities of the two types (and sizes) of the powders are within a specified percentages, a slide shuttle 14 is moved to catch on the shuttle the residual or unsettled mixed powder of nearly equal settling velocities. These equal-settling mixed powders in suspension are separated for immediate metallizing use while the already settled powders are drained through the valve 15 for subsequent reuse.

The above method of minimizing gravitational segregation is useful not only in ceramic metallizing, but also in painting, depositing, injecting, mixed food preparation, or plasma spraying with multiple nonreacting solid or liquid materials of differing densities suspended in a gas or liquid.

Useful metallizing compositions include the commonly used W:Fe or Mo:Mn system containing 10 to 30 weight percent of Fe or Mn, or their derivatives $WO_3$:$Fe_2O_3$, $MoO_3$:$MnO_2$, or other non-oxide systems. From the atomic or molecular weights of the elements W, Mo, Fe, Mn, O, Cl, F, I, Br, . . . or radicals $NO_3$, $SO_4$, . . . , the weight percentage of the heavy metal W or Mo and the other braze and melting temperature-lowering metals such as Cu, Zn, Pb, Sn, Sb, Bi, Fe, Mn, Ag, Au, In, . . . used for the paste, suspension, or solution metallizing compositions can be readily determined. Generally, I maintain the same ratio of 10 to 40 weight percent of braze metal to the 90 to 60 percent of heavy metal in these compositions.

The principle of control of the segregating mixed powders may be used in other industrial process, such as painting, powder mixing, or plasma spraying to achieve more uniform results. In plasma spraying of mixed powders, one has to consider not only vertically downward gravitational segregation of the settling powders in a gas medium, but also the propulsive forces of the high-velocity plasma gas jets acting usually horizontally to propel the powders to reach the target spray areas with uniform mixed powder compositions.

There are other ways to insure a substantially constant chemical composition consisting of at least two types of metallizing materials having different densities and carried in a fluid suspension medium. One way is to cause the two types of materials to come out of the suspension medium in a substantially constant chemical composition thereby ensuring uniformity and reproducibility of the metallizing results. For example, the two types of materials may be integrated into physically integral and inseparable forms, such as by alloying the materials into integrated alloy form, or coating the internal and/or exterior surface of one type of material particles with the other material to form integrated coated powders.

Thus, tungsten particles may be alloyed or coated with iron to form integral or inseparable W—Fe powders. Similarly molybdenum powders may be alloyed or coated with manganese to form integral Mo—Mn powders that will not segregate.

Another method to minimize segregation of a single fluxing (e.g., MgO, $Y_2O_3$) or brazing (e.g., Cu, CuO, Zn, ZnO), co-metallizing (e.g., Mn or $MnO_2$ with Mo or Fe or $Fe_2O_3$ with W) material is the use of an aqueous or other solution of W and/or Mo compounds such as sodium molybdate or tungstate which is soluble in water, or $MoO_3$ or $WO_3$ which is soluble in hot water particularly in the presence of $NH_4OH$. Here, the solution is the settling medium itself and suspended powders being of a single type, cannot segregate. Solutions of compounds of Cu, Zn, Fe, Mo, . . . used with powders of W, Mo, $WO_3$, or $MoO_3$ achieve the same results.

Yet another method to minimize segregation of a metallizing or metallizing and brazing composition is to sequentially deposit or co-deposit the various metallizing and/or brazing metals on a ceramic powder, such as diamond, carbon, alumina, zirconia, or silicon carbide. The depositing may be by chemical or physical methods such as vacuum evaporation, sputtering, ion plating, electrolytic or electroless plating, chemical vapor deposition, plasma spraying of metals or metal compounds. The heated ceramic powders may also be fluidized in an atmosphere of the metal halides, organometallic compounds, or other suitable gaseous medium flowing in a suitable processing chamber. The processing chamber may even be heated to a metallizing/brazing temperature so that the resultant fluidized product may be specially pre-coated, but non-bonded or non-aggregating powders that may later be bonded at lower temperatures by, for example, a In—Sn or Pb—Sn low-temperature soldering process. Such a procedure is particularly suitable for mounting low-melting ceramics or glasses, or delicate electronic circuits. All of these components cannot be processed at the usual high metallizing temperatures.

To completely eliminate gravitational segregations, solution metallizing is the ideal process. Many molybdenum and tungsten compounds are soluble in water, alcohol, acid, or bases. $MoO_3$, for example, is soluble in hot or ammoniated water. Oxide, chloride, nitrate, sulfate, halogen, and other compounds of iron, manganese, nickel, antimony, lead, tin, copper, zinc, and bismuth are similarly soluble. Mixtures of W/Mo and the other solutions may be compounded into proper compositions for the metallization of various ceramics. The use of solutions of compounds, e.g., halides, of nickel, lead, tin, zinc, and copper allows these metal compounds to be reduced in a hydrogen or nitrogen/hydrogen atmosphere to supply the braze metal. In a single processing step, then, complete metallizing, brazing, and bonding is possible.

One difficulty of metallizing a ceramic such as MACOR, Corning Glass's machinable glass ceramic, by the solution method is the relatively low, allowable metallizing temperature of about 950° C. The solubilities of the metallizing compounds are also restricting factors. Still, many potential metallizing compounds are soluble or at least partly soluble. Zinc chloride and sodium molybdate, for example, are soluble up to 432 and 65 grams, respectively, per 100 cc of cold water. Such a composite solution may be filtered to remove solid particles and used for metallizing various ceramics.

Useful W/Mo-based metallizing compounds include: X (X=W or Mo), $XO_3$, $Na_2XO_4$, $K_2XO_4$, $Li_2XO_4$, and XH (H=$F_2$, $Br_2$, $Cl_2$, and $I_2$). Useful braze metal compounds include: many YNO$_3$, YZ (Y=Cu, Ag, Au, Zn, In, Fe, Ni, Mn, Ga, Sn, Pb, Cd, Tl, . . . , and Z=F, Br, Cl, and I). Many of these compounds are soluble in water, alcohol, or other organic or inorganic solvents and can, therefore, be used to prepare metallizing solutions. Knowing the elemental atomic weights, one can readily compute the weight of metallizing W or Mo or braze metal in each gram of these chemical compounds.

Another important consideration in making dissimilar materials joints relates to thermal mismatch stresses and strains. In any ceramic-metal joints, or for that matter, any joining of two dissimilar materials or even within a single-phase homogeneous material, the matching or mismatch of their thermomechanical characteristics in general, and thermal expansion coefficients in particular, is extremely important. From this mismatch of their thermal expansions, thermal stresses are generated.

Mismatches in other thermomechanical characteristics also result in other thermomechanical mismatch stresses and strains. The magnitude of these mismatch stresses and strains determines the failure probability of the joint.

Thermally generated mismatch stresses and strains are critical factors in dissimilar materials joints. In metal-ceramic joints, differences in coefficients of thermal expansion (CTE) between the metal and the ceramic produce thermal-mismatch stresses and strains. These mismatch stresses and strains must be carefully controlled.

According to Hagy and Ritland's paper on "Viscosity Flow in Glass-to-Metal Seals," J. Amer. Ceram. Soc., Vol. 40, pp. 58–62, 1957, the CTE mismatch differentials of within 100 ppm (parts per million) are considered as allowable.

However, such CTE mismatches relate to only the static, or thermal equilibrium, case. They do not truly represent dynamic or transient conditions when the joint is being heated or cooled. Yet such transient or dynamic conditions always exist during the manufacture or service of the joint.

An important problem with common joining processes is the understanding and control, over a period of time, of dynamic mismatches in temperatures, CTEs, and thermal strain and stress profiles and gradients in the joint region. This specification describes such dynamic mismatch phenomena and proposes special, laterally graded composition and/or physical property profiles of the joint region.

As will be shown, the computed dynamic mismatches in expansion strain may, if unrelieved, exceed the yield points of even the metallic joining materials. The dynamic mismatch stresses also often exceed the flexure or even comprehensive strengths of the ceramic materials. What fails most metal-ceramic joints, or causes most ceramic coatings to crack, peel, flake, or spall, is, therefore, the dynamic, rather than the static, thermal expansion mismatch. Through this dynamic mismatch approach, one can determine the location, magnitude, and occurrence time of the maximum dynamic mismatch stresses and strains. One can also devise simple procedures to estimate the joint strength and to reduce these critical stresses and strains on the relatively weak ceramic.

The linear CTE (f) is defined as the thermal expansion per unit length per degree Celsius. It refers to only the static or thermal equilibrium case. For a given material, this coefficient is a constant for a temperature range of interest. Within this range, therefore, the CTE does not depend on the initial and final temperatures, specimen geometries, sizes, diffusivities, or surface characteristics, and heating or cooling rates and other conditions. Each material has a single, unique static CTE for a given temperature range.

During a cool-down process, the static thermal shrinkage (or negative expansion) strain (e) for a given material is, by definition, the static CTE (f) multiplied by the cooling temperature range ($\Delta u$):

$$e = f \times \Delta u$$

For a steel rod with a CTE of $f_s$ cooling through a temperature range of $\Delta u_s$, this strain is $e_s$. Similarly, for a rod of Macor (Corning's machinable glass ceramic) with a CTE of $f_m$ cooling through a temperature range of $\Delta u_m$, the shrinkage strain is $e_m$.

Macor is machinable on conventional metalworking machines. The key to its machinability is its two-phase microstructure of randomly oriented mica microcrystals in a glass matrix. During machining, cracks are propagated in the direction of the applied force. These cracks are deflected by the microcrystals to the surface. According to Corning, Macor has a CTE of about $9.35 \times 10^{-6}$ °C.$^{-1}$, and can be sealed to 52% nickel alloys, chrome-iron stainless steel, platinum, and other materials by using a special glass frit from Corning.

In the static case, the materials of a steel and Macor joint are always in constant thermal equilibrium. That is, $u_m = u_s$ for all t. At the beginning of cooling (time t=0), both materials are at the same brazing temperature of $u_0$. At any time t during the cooling after the joining by, e.g., brazing, the cooling temperature ranges for steel and Macor are always the same in the static case. Thus:

$$\Delta u_m = u_0 - u_m = u_0 - u_s = \Delta u_s = \Delta u$$

Usually, we assume that both the steel and Macor are homogeneous, defect-free, and perfectly joined together. In addition, the static thermal mismatch strain is not relieved, modified, or adjusted in any way. In this simple case, this static mismatch strain between steel and Macor is:

$$\Delta e = e_s - e_m = (f_s - f_m) \times \Delta u = \text{constant} \times \Delta u.$$

Dynamic mismatches result from the fact that metals and ceramics have widely different thermal conductivities. (The conductivities of metals (at 273.2K) vary from 0.0208 W/(cm K) for tellurium, to 4.29 for silver W/(cm K), while those of ceramics (at 311K, excluding diamond) are from 0.029 W/(cm K) for PbO to 2.27 W/(cm K) for beryllia.) During heating of a metal-ceramic joint, the temperature of the ceramic lags behind that of the metal, often markedly so; during cooling, the opposite is true. This produces different temperature profiles in the metal and ceramic at a particular time on either heating or cooling. Dynamic mismatches in temperatures, effective CTE's, thermal strains (i.e., expansions on heating or shrinkages on cooling), and thermal stresses (strains multiplied by Young's moduli) then result.

In reality, after the actual brazing to produce the metal-ceramic joint, only at the beginning of the cooling (t=0) are the two materials at the same brazing temperature of $u_0$. At any subsequent cooling time after the brazing (t>0), the ceramic is at a higher temperature than the metal. There is therefore a non-zero dynamic temperature differential ($\Delta u$).

Consider the special case of a long metal rod joined end-to-end to a long ceramic rod of the same diameter, D=2r. The metal is SAE 1010 carbon steel, while the ceramic is Macor. The joint is brazed at 950° C. and is, for a worst-case condition, suddenly air quenched in a 20° C. environment.

The following assumptions are made in the computation of the dynamic or transient mismatch stresses and strains:

The steel and Macor cylinders are infinitely long and have only separate and independent, radial heat conduction. There is no axial heat flow from one material to the other.

Biaxial or triaxial stresses and strains are not considered.

Only elastic strains and stresses are treated.

Strain and stress relief through plastic deformation or other mechanisms is ignored.

Both materials are homogeneous and free of any defects such as pores, voids, microcracks, inclusions, or second phases.

The two materials do not have elemental interdiffusions, undergo phase changes, or otherwise suffer modifications in physical and chemical properties.

There are no intervening bonding material layers of different chemical, thermal, and mechanical properties than those of the steel and Macor.

In a metal-to-metal joint, the assumption of pure radial-heat conduction in the cylinders is obviously not valid. However, if one or both cylinders are made of thermally insulating materials such as ceramics, this assumption is a good start. Mainly because of the radial-heat conduction assumption, the temperature in each cylinder is uniform at a given radius. To provide a more detailed analysis, if any one or more of these assumptions were not made, would be extremely difficult. At this time, the comparative errors from the above assumptions are not known, even qualitatively. Hence, any expensive, time-consuming analysis is not justified.

The Fourier equation for independent radial-heat conduction in long metal and ceramic cylinders is well known. The solution of the cylindrical heat-conduction problem consists of an infinite series. Each term of the series is a product of a Bessel's function and an exponential function, as given in various textbooks on heat conduction. Data tables and master charts for cylindrical heat diffusion have been compiled. See, e.g., 1961 Gebhart's "Heat Transfer," McGraw-Hill, New York). One can thus determine the temperature profiles at different locations (i.e., radial position r] in a cylindrical end-to-end joint) at various times. At the critical time ($t_c$) the critical profile of the temperature differentials and the associated, maximum transient dynamic thermal-mismatch stresses and strains obtain.

Table 1 gives the step-by-step temperature changes of a 5.08-cm diameter, cylindrical end-to-end steel-Macor joint for the temperatures of steel and Macor, respectively, at the cylindrical axes (r=0) for t=0 to 41,800 s after cooling from the brazing to near room temperatures. The computer simulation results in Table 1 also give the maximum temperature differential between steel and Macor at the axial center point (i.e., $\Delta u = u_m - u_s$) at different cooling times.

Immediately after brazing (t=0), this differential is zero because both the steel and Macor are at the same brazing temperature of 950° C. Subsequently, faster cooling of the steel increases this differential, reaching a maximum of 755° C. at t=1,000 s. After both rods are significantly cooled, the temperature differential decreases. Beyond 29,900 s (8.3 h), for example, both rods are near room temperature at 20° C. The maximum temperature mismatch or differential of 755° C. at t=1,000 s produces the maximum or critical dynamic mismatch stress and strain.

By comparison, for a 2.54-cm diameter steel-Macor joint, the maximum temperature mismatch of 727° C. at the axial center occurs sooner (i.e., at 440 s) after cooling.

The dynamic thermal expansion coefficients (f*) and the resultant dynamic thermal mismatch strains ($\Delta e^*$), and stresses (s*) strongly depend on the joint materials, geometries, sizes, physical and surface properties, and heating or cooling conditions. Starting with zero strain on cooling from the brazing temperature of 950° C. the dynamic strain in the steel rod is $e^*_s = f_s \times \Delta u_s$, while in the Macor rod, $e^*_m = f_m \times \Delta u_m$, where $\Delta u_s \neq \Delta u_m$. The difference in dynamic mismatch strain is $$\Delta e^* = f_s \times \Delta u_s - f_m \times \Delta u_m.$$

Under the pure cylindrical heat-conduction model, the computed dynamic or transient mismatch strain reaches a maximum of about 0.0123 at t=1,000 s. Such a high strain, if not relieved or reduced, would exceed the yield point of the steel, which is joined to the even more rigid Macor.

The dynamic (or effective) CTE mismatch ($\Delta f^*$) can be computed by dividing the dynamic mismatch strain ($\Delta e^*$) by the average cooling temperature range [$\Delta u_v = 950 - (u_s + u_m)/2$]. For the 5.08-cm steel-Macor end-to-end joint cooling from 950° C. to 20° C., this dynamic CTE mismatch depends greatly on the cooling time and conditions. A maximum computed dynamic CTE mismatch of about 29.6 $10^{-6}$ C.$^{-1}$ occurs at a cooling time of 90 s. Such a high dynamic CTE mismatch is intolerable according to the Hagy and Ritland criterion mentioned above.

For the 5.08-cm steel-Macor rod joint cooling from 950° C. to 20° C. the computed effective or dynamic CTE mismatch, $\Delta f^* = (f^*_s - f^*_m)_{av}$, is more than two to five times greater than the corresponding mismatches for the static or equilibrium case, for cooling times of 10 s to 6,000 s. This ratio of dynamic CTE to the static CTE reaches a maximum of 5.3 at t=75 s.

To compute the dynamic mismatch stresses, one may further neglect the presence of the braze and the metallized layers, and use a Timoshenko approach as follows. Consider a portion of the steel specimen of unit length and unit cross-section, brazed together with a Macor specimen of equal length and cross-section. At time after cooling from the brazing temperature, the temperature of the steel is $u_s$ and $\Delta u_s = 950 - u_s$, while the temperature of Macor is $u_m$ and $u_m = 950 - u_m$. The steel specimen has thus shrunk from unit length to $1 - f_s \times \Delta u_s$, while the Macor has shrunk to $1 - f_m \times \Delta u_m$. The steel has shrunk more than Macor, since both $f_s$ and $\Delta u_s$ are greater than $f_m$ and $\Delta u_m$, respectively. To maintain joint integrity, the originally stress-free but overshrunk steel must be stretched with dynamic tensile stress s by the adjoining Macor to length y from length $1 - f_s \times \Delta u_s$, while the undershrunk Macor must be compressed with dynamic compressive stress $s_m^*$ by the steel to the same length y from length of $1 - f_m \times \Delta u_m$. Hence, the tensile stress in the steel is $$s_s{}^*=E_s\times(y-1+f_s\times\Delta u_s)/(1-f_s\times\Delta u_s)$$

where $e_s$ is the Young's modulus of steel ($2.11\times10^4$ kg/mm$^2$).

The compressive stress in Macor is $$s_m{}^*=E_m(1-f_m\times\Delta u_m-y)/(1-f_m\times\Delta u_m)$$

where $E_m$ is the Young's modulus of Macor ($3.52\times10^4$ kg/mm$^2$).
Apparently, $s_s{}^*=s_m{}^*$. Hence, $$y=[(1-f_m\times\Delta u_m)E_m+(1-f_s\times\Delta u_s)]/(E_s+E_m)$$

The maximum computed stress exceed 37.1 kg/mm$^2$ well above Macor's flexural strength of 10.5 kg/mm$^2$ or even its comprehensive strength of 35.2 kg/mm$^2$.

Statically, Macor only marginally "matches" a few low-expansion metals. Because of the high dynamic mismatches in CTE, strain, and stresses, the inadequate mechanical strength and thermal resistance of most conventional metal-ceramic joints in general, and steel-Macor joints in particular, are not surprising. Also, dynamic mismatch stresses, not static ones, usually fracture the brazed metal-ceramic joint.

Measures must therefore be taken to reduce the dynamic mismatch stresses on the relatively weak ceramic so that the ceramic is no longer subjected to the high stresses. This reduction can be achieved by, e.g., absorbing a major portion of the dynamic mismatch stresses normally present in the ceramic through the use of a soft, yieldable metallic braze. These measures prevent the brazed joint failures particularly from these dynamic mismatch stresses, because residual or actual mismatch stress between the two joined materials is the theoretical mismatch stress with a portion thereof absorbed in the metallized or brazed layer.

Specifically, this invention also describes the following methods, for uses singly or in combination, to minimize or neutralize these high mismatch stresses and strains:

1) Using a soft, yieldable metal layer to braze the metallized ceramic to the metal, and to absorb within the braze layer a large or major portion of these mismatch stresses so that the relatively weak MACOR or other ceramic is no longer subjected to high stresses thereby preventing fractures;
2) Radially grading, rather than axially or longitudinally grading bonding interfacial region, the thermal conductivity (or reciprocal of thermal resistivity), thermal expansion coefficient, and tensile strength of the braze metal, to ensure that the maximum residual mismatch stress, after absorption in the braze or the shock-absorbing interfacial region to be described below, will not exceed the local material strength in the ceramic at any point and time;
3) Axially grading, or controllably changing, from the ceramic side toward the metal side, the thermal expansion coefficient of the braze layer to minimize direct mechanical interaction between the steel and ceramic members;
4) A toughened and strengthened microengineered interfacial region between the ceramic and metallized layer to absorb thermomechanical shocks;
5) A new method to achieve flawless bonding regions;
6) Controlled cooling of the liquid braze layer to achieve radially outward solidification and elemental segregation for the desired patterns of radial grading properties (FIG. 6);
7) Using as the braze layer a plurality of strength columns of small lateral dimension L, embedded in a matrix of soft metal to minimize expansion differential, which is the product of L and the thermal expansion coefficient differential (FIG. 7);
8) Using elongated reinforced fibers or sheets placed along the potential fracture path and variably oriented along the local tensile fracturing stresses (FIG. 8); and
9) Combining radial grading with the conventional axial grading to change the thermal expansion coefficient of the braze layer from the ceramic side toward the metal side, to minimize direct mechanical interaction between the metal and ceramic members.

The first two objectives are achieved by providing a novel composite metallic braze layer or disc consisting of a central copper core inside an outer copper alloy ring or washer made of, e.g., 70:30 Cartridge brass. This composite metallic disc joins together a ceramic body and a metal body. This disc is parallel to and forms part of the bonding interfacial region, and has, for example, a pure copper central core placed inside the opening of an outer 70:30 cartridge brass ring or washer. The CTE of pure copper is $16.5\times10^{-6}$ °C.$^{-1}$, while that of the cartridge brass is $19.9\times10^{-6}$ °C. Also, the Young's modulus of the brazing-annealed, dead-soft pure copper is much lower than that of the cartridge brass. The thermal conductivity of pure copper central core at 0° C. is 4.03 W/(m.K), while that of the outer cylindrical tube with 30% Zn in Cu is 1.14 (W/m.K).

The combination of high thermal conductivity and low CTE and Young's modulus in the core region of the joint achieves the required results. In a steel-ceramic joint, the maximum dynamic mismatches in temperatures, CTEs, and thermal strains or stresses occur at the axial centers of the interfacial region. A dead soft, brazing-annealed, pure copper therefore occupies the core region. This copper has a small Young's modulus, and a yield strength less than the fracture strength of the ceramic. It is easily deformable to absorb and relieve much of the dynamic mismatch thermal strains and stresses. Pure copper also has relatively low CTE to reduce these mismatch effects in the first place. In addition, the copper is a good thermal conductor, equalizing the temperature between the metal and ceramic to further minimize mismatch strains and stresses.

On the other hand, the periphery of the braze disc is made of relatively more expansive but thermally lower-conducting 70:30 brass. At the peripheral region, the mismatch temperature differentials are relative small. The higher Young's modulus of the cartridge brass is even desirable at the peripheral region to enhance the joint rigidity.

This composite braze disc design will thus provide the radially graded profiles of braze composition, CTE, ductility, and thermal conductivity needed to minimize the critical dynamic-mismatch.

The composite braze metal discs can also be made by multiple printing, metallurgically cladding or mechanically press-forming a sphere or disc inside a washer, or by slicing concentric metal tubes of graded compositions with a solid pure metal core.

Elemental interdiffusion during the braze manufacture, brazing operation, or special pre- or post-brazing heat-treatments produce more diffused composition profiles in the braze discs and leads to efficient lateral-grading results for a given transverse size of the bonded region. More description of the radially graded seals are given in my U.S. Pat. No. 4,890,783.

To practice this lateral grading invention, skilled persons can, of course, select other yieldable metals such as gold, silver, tin, lead, indium, zinc, iron, nickel, or other materials to replace copper, and select other chemical elements to replace the copper-strengthening zinc. The resultant new alloys will, of course, be different in compositions, strengths, diffusivities, thermal conductivities, melting or softening points, and other properties.

Cu—Ag, Cu—Al, Cu—As, Cu—Bi, Cu—Ca, Cu—Cd, Cu—Fe, Cu—Li, Cu—Mg, Cu—Mn, Cu—Ni, Cu—P, Cu—Pd, Cu—Pt, Cu—S, Cu—Sb, Cu—Si, Cu—Sn, Cu—Te, Cu—Ti, Cu—Zr can be similarly used to minimize dynamic mismatch stresses. Alloys of Ag, Al, Au, Bi, Cd, Co, Cr, Ge, Fe, Ir, Li, Mg, Mn, Mo, Ni, Pb, Pd, Pt, Rh, S, Sb, Si, Sn, Ta, Te, Ti, V, W, Zn, Zr, rather than Cu, are also useful. Higher-melting braze metals may also be used for high-temperature structural metal-ceramic joints.

My lateral grading technique produces graded metal-ceramic microjoints in parallel, while the conventional axial grading technique produces graded metal-ceramic microjoints in series. The optimum combination of the two lateral and axial grading can be analyzed by simulation techniques. Even electrical analog techniques can be used to determine the optimum combination of parallel and series microjoints by arranging electrical resistors or capacitors in various parallel/series combinations, either in actual experiments or on the computer.

All the above measures increase the ratio of the ceramic material strength to the dynamic and/or static mismatch stresses due to differential temperatures and thermal expansions so that these mismatch stresses do not exceed the ceramic material strength at any point and time thereby preventing bond failures.

The computation of the dynamic mismatch stresses provides a new approach for developing non-destructive testing (NDT) procedures. Since stresses are stresses no matter how they originate. Stresses due to externally applied loads, internal residual stresses, phase transition-induced stresses, thermal mismatch stresses, and their combinations all cause the weaker ceramic to fail, precisely when the combined stresses exceed certain fracture strength of the ceramic. This failure always occurs at the moment of maximum temperature differentials between the metal and ceramic.

Hence, qualitatively, the higher the allowable air or water quench temperature or severity, the higher the actual dynamic-mismatch stress and joint strength. From the above dynamic mismatch study, there is even a calculable maximum "mechanically equivalent stress" from each quench treatment.

Under standardized cooling or quenching conditions, such as rapid (e.g., within 0.5 second) 20° C. air cooling or ice water quenching, there is a one-to-one correspondence between the joint strength (at, e.g., 20° C.) and the allowable initial cooling or quenching temperature. This temperature can thus be a direct measure of the mechanical strength of the joint with a specific joint configuration (e.g., cylindrical, end-to-end) and size (e.g., 5.08 cm in diameter). Hence, some selected quenching and mechanical testing results will provide a useful date table correlating the quenching temperature and/or severity with the joint flexure strength for use in NDT testing.

Standard tensile or flexure tests are often difficult for metal-ceramic joints because of the critical jigging, sample alignment, and loading requirements. Actual metal-ceramic joints often also have complex geometries, and special material, size, or composition and property profile combinations. All these conditions can make the standard mechanical test results difficult to reproduce and extrapolate to actual service conditions, or to determine if valid specifications have been met.

Yet, a controlled cooling or quenching test is simple and fast. It can be applied to a joint of any practical shape and size. There are no errors due to sample jigging, aligning, and loading. Nor are there any unknown joint damages due to handling prior to or during the actual testing. The results are often more relevant and immediately useful without extrapolations as to sizes, shapes, joint configurations, and thermal shock environments. In addition, the test is non-destructive if the specimen meets the specification. It is particularly useful and cost-effective for the following cases:

1. Joints of complex geometries and shapes.
2. Very large or small samples.
3. Joints of combinations of materials with widely different mechanical properties.
4. Joints that fail under dynamic cooling or heating conditions, which are difficult to duplicate on standard testing machines.
5. Joints of delicate parts which are hard to jig, align, or load. For example, it would be not only very costly but difficult to develop the necessary equipment and procedure for determining the bond strength of an irregular diamond crystal bonded onto a copper substrate for electronic heat sink applications.
6. Peeling, spalling, microcracking, and adherence to substrates of thin films.

TABLE 1

| Nonsteady Heat Transfer Computations For a 2-inch MACOR-Steel Joint Cooling from 950° C. to 20° C. | | | |
|---|---|---|---|
| t | $u_m$ | $u_s$ | $u_m - u_s$ |
| 0.0 | 950 | 950 | 0 |
| 6.0 | 950 | 947 | 3 |
| 12.0 | 949 | 935 | 14 |
| 23.9 | 949 | 901 | 48 |
| 35.8 | 949 | 867 | 82 |
| 47.8 | 948 | 835 | 113 |
| 59.8 | 948 | 804 | 144 |
| 89.6 | 948 | 731 | 217 |
| 119 | 947 | 665 | 282 |
| 239 | 935 | 456 | 478 |
| 358 | 918 | 316 | 703 |
| 478 | 901 | 220 | 681 |
| 598 | 884 | 155 | 729 |
| 717 | 868 | 112 | 756 |
| 836 | 851 | 82 | 769 |
| 956 | 835 | 62 | 773 |
| 1200 | 804 | 39 | 765 |
| 1792 | 731 | 23 | 708 |
| 2390 | 665 | 22 | 643 |
| 3580 | 551 | 22 | 528 |
| 4780 | 456 | 21 | 436 |
| 5980 | 379 | 21 | 358 |
| 7170 | 316 | 21 | 296 |
| 9560 | 220 | 21 | 199 |
| 12000 | 155 | 21 | 134 |
| 14300 | 112 | 21 | 91 |
| 19100 | 62 | 20 | 42 |

TABLE 1-continued

Nonsteady Heat Transfer Computations
For a 2-inch MACOR-Steel Joint
Cooling from 950° C. to 20° C.

| t | $u_m$ | $u_s$ | $u_m-u_s$ |
|---|---|---|---|
| 23900 | 39 | 20 | 19 |
| 29900 | 27 | 20 | 7 |
| 35800 | 23 | 20 | 3 |
| 41800 | 21 | 20 | 1 |

Figure 6:
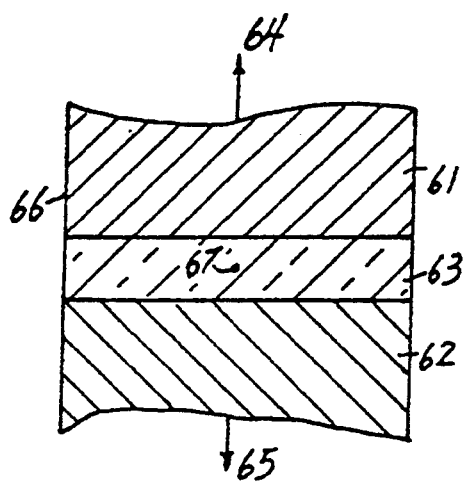
FIG. 6 shows a cooling method after metal-ceramic bonding to achieve controlled solidification and elemental segregation for overcoming dynamic mismatch stresses.

By properly controlling the cooling of a metal-ceramic joint, the desired lateral grading effect can also be achieved. For example, as shown in FIG. 6, after the joining of a metal cylinder or cylindrical plate 61 to a ceramic cylinder or cylindrical plate 62 of about the same diameter, the cylindrical surfaces are insulated thermally or cooled slowly relative to the free or unjoined ends. Heat is then extracted mainly axially at these ends 64 and 65. The center 67 of the bonding regions is thus cooled fast and solidified first. The solidification therefore propagates radially outward. According to the Ag—Cu phase diagram, in a Ag—Cu alloy braze disc, the first-freezing center portion has relatively pure Ag or Cu metal, if the original alloy composition contains less or more, respectively, than 28 weight percent of Cu. According to the theory of alloy solidification, subsequently solidifying and expanding hollow cylinders in the resultant braze disc will be less and less pure in Ag or Cu. The last solidifying, outer cylindrical surface layer will be the Ag—Cu. The eutectic containing 28% (by weight) of Cu and 72% of Ag. Thus, the physical properties are laterally graded, by solidification, in the solidified braze disc. The central relatively pure metal portion of the bonding region will be softer and more thermally conductive than the peripheral eutectic region. By selecting a suitable initial braze composition, the center can even also have a smaller thermal expansion coefficient than the peripheral eutectic, achieving maximum reduction in dynamic mismatch stresses.

This controlled cooling method is particularly effective with large, flat joints when the ratio of diameter or lateral size is large relative to the length or thickness, facilitating central axial cooling first.

Figure 7:
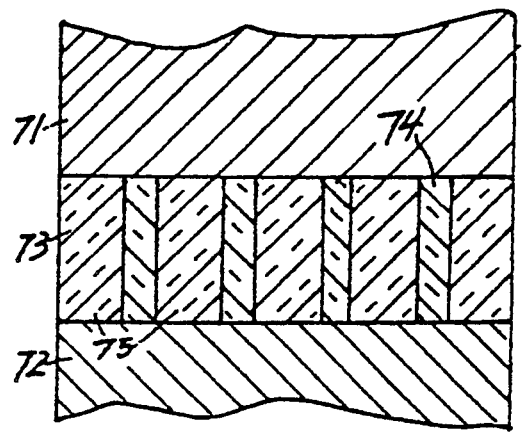
FIG. 7 shows a new method of overcoming mismatch stresses.

FIG. 7 shows a joint between a metal 71 and a ceramic 72 whose braze layer 73 consists of a plurality of load-carrying strong columns 74 (e.g., 70:30 Cartridge brass) embedded in a relatively soft matrix 75 of pure copper. Since the individual strong, load-carrying columns 74 have minimal lateral dimensions (a few millimeters or less), the thermal mismatch expansion strains and stresses are small.

Figure 8:
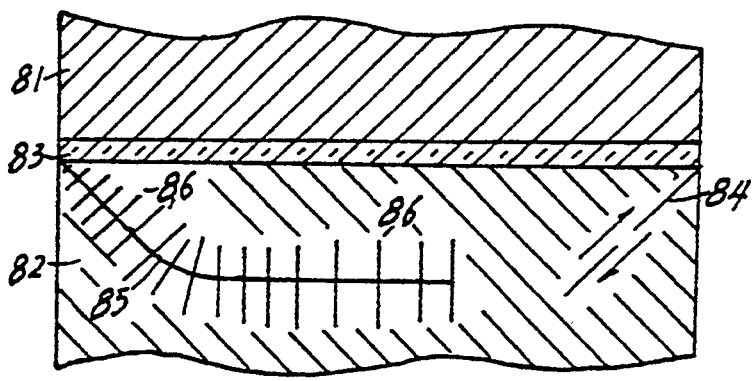
FIG. 8 shows another composite structure involving reinforcing fibers strategically positioned and oriented to overcome interfacial surface failures in the ceramic.

FIG. 8 shows the usual failure patterns in a metal (81)-ceramic (82) joint, or coating of ceramic on metal, due to mismatches that result in debonding, cracking, blistering, peeling, and spalling. The initial crack occurs at the peripheral surface between the metal (including braze 83) and ceramic 82 and is inclined at 45° to the horizontal. The mismatch stresses are tensile in the metal 81 but compressive in the ceramic 82. The compressive stress induces a shear which is maximum at the 45° plane 84 (see the right side of the figure). The crack or fracture thus initiates at 45° but levels to horizontal. By placing elongated reinforcing members 86 such as strengthening carbon fibers or weaved sheets 86 in the Al$_2$O$_3$ ceramic 82 along the fracture path in varying directions locally normally of the tensile stresses to best overcome the tensile mismatch stresses along the fracture path 85, the failure may be prevented. Note that in the left side of FIG. 8, the directions of the elongated reinforcing fibers change from 45° at the metal-ceramic interface to nearly vertical deep inside the ceramic 82.

Another method to overcome dynamic stresses is to grade the composition, and therefore the thermal expansion coefficient and other physical properties in such a way that the local composition gradient is roughly proportional to the local temperature gradient. There are four cases to be considered for this functional grading:

1. Maximum critical dynamic stresses occur when the ambient-exposed surface is rapidly heated with a constant ambient temperature heating, such as inserting a ceramic-metal bond into a constant-temperature hot or furnace environment;
2. Maximum critical dynamic stresses occur when the outer surface is rapidly heated with a fixed quantity of heat, such as during high-intensity, constant-power pulsed laser or electron beam pulse or pulses;
3. Maximum critical dynamic stresses occur when the outer surface is rapidly cooled with a constant ambient temperature bath, such as when the ceramic-bond joint is rapidly quenched in, e.g., air or water of constant temperature;
4. Maximum critical dynamic stresses occur when the surface is rapidly cooled by taking away a fixed quantity of heat, such as applying a fixed quantity of water for rapid evaporation and heat absorption per unit area of the outer surface.

In the thermal or the equivalent material diffusion art, cases 1 and 3 are "infinite source" diffusions and give error function complement (erfc) solutions, while cases 2 and 4 are "constant-source" diffusions and give exponential function for their solutions. To overcome dynamic mismatch stresses due to transient thermal heating, I functionally grade the material compositions as to the major alloying element or elements, decreasing the thermal expansion coefficient or increasing the strength in proportion to their content such that the surface composition is also either error-function complementally graded or exponentially graded in the proper direction, respectively for cases 1 and 3, or 2 and 4. For cases 1 and 2 where heat is applied, I shall add the major element or elements to in-diffuse, while for cases 3 and 4, I shall subtract the major elements (i.e., with getter material) to out-diffuse material. For infinite material sources, I use constant-concentration ambient such as unlimited supply of gaseous, liquid, or solid diffusing material. For constant material sources, I use limited or fixed quantity of diffusing material. For in-diffusion, I use diffusant materials, while for outdiffusion, I use gettering material to get or remove from the surface the major elements.

After the material surface diffusion or outdiffusion treatment, with a constant or infinite source, the resultant surface composition profile or critical physical property profile will be similarly shaped (i.e., exponentially or erfc graded) like the anticipated maximum critical transient temperature profile. This condition insures that the local maximum stress never exceeds the local material strength at any time, and thus best withstands the transient thermal stresses due to this type of transient heating or cooling.

The above two and other methods of overcoming dynamic mismatch stresses are not only useful for dissimilar material joints, but for even a single-phase homogeneous material subjected to critical thermal surface profiles, such as when a carbon-carbon composite is subjected to high-intensity laser pulses, or severe surface quenching when hot.

Each metal-ceramic joint or bond must be specially designed. The factors in joint design include metal and ceramic composition, joint failure modes, parts shapes and sizes, thermal and other requirements. The requirements for the National Aero-Space Plane (NASP) is totally different from those of the diamond heat sinks or fusion reactors. A ceramic-metal bond designed for maximum mechanical strength is usually not the best for thermal conductances, which is critical in heat sinks. What is best for one application (e.g., for preventing rapid heating failures) may even be precisely the worst for another (e.g., for preventing severe quenching failures), as shown by the functional grading technique described in this application. On the NASP, for example, the best titanium-$Si_3N_4$ joint for the turbine subjected to rapid heating should not be used for the wings of the same plane subjected to possible ice quenching failures. A joining method for many conditions may not be the best for any application.

If all these measures are still insufficient to prevent dynamic thermal mismatch failures, the conventional axial elemental grading or sudden composition changes may be added. One method consists of providing a disc of low-expansive metals such as Sylvania #4, Dumet, 50% nickel alloy, chrome-iron, stainless, platinum, Sealmet, and titanium placed between he steel and the copper braze. In this way, the ceramic MACOR is mechanically isolated from the highly expansive steel. The desired elemental profiling can also be achieved through controlled diffusion.

In addition to achieve metallizing uniformity and minimal mismatch stresses, I have also found it desirable to microengineer the chemical compositions, microstructures, and mechanical properties of the bonding interfacial regions between the ceramic and metallized layer. Merely perfecting the interfaces surfaces alone, as is commonly done, is inadequate to produce strong and reliable joints for withstanding the unavoidable, severe mismatches stresses and strains as shown above.

Different physical, chemical, and electrical metallizing or film-forming methods have been developed for metal-ceramic bonding. Each has its unique advantages. Some, for example, are atomically precise. Others thoroughly clean the substrate surfaces for better adhesion. Some others result in crystalline epitaxy, which is necessary for semiconductor or other devices. Others produce splat cooling and superfine grains, with resultant enhanced mechanical properties, for example, increased Young's modulus. Still others are done at low temperatures to avoid unwanted thermal effects. But none deal effectively with the critical problem of thermal mismatch stresses and strains.

For extremely shock-resistant joints or metallized layers, I have found it absolutely necessary to have a carefully microengineered interfacial layer between the ceramic and the metallized layer. This layer is designed to absorb the major portion of the always present mismatch stresses and strains. Many of my ceramic metallizing processes typically last more than 20 minutes and involve liquid-forming layers containing, directly or indirectly, $MoO_3$ which melts at 801° C., and $WO_3$ which melts at about 1,550° C. This melting point can be further reduced by alloying with other compounds of metals such as CuO, SnO, $Ag_2O$, $Sb_2O_3$, $Bi_2O_3$, ZnO or PbO. The reduced metal becomes molten, to freeze as the dead-soft annealed braze metal.

Liquid diffusion is rapid with diffusion coefficient $D_l = 1\,E-4$ to $1\,E-5\,cm^2/sec$. Processing for t=20 minutes gives a diffusion length of up to the square root of $D_l \times t = 0.35$ to 0.11 cm. In addition, a diffused interfacial layer of graded composition, microstructures, and mechanical properties is formed which can be highly shock-absorbing.

In contrast, most conventional bonding or coating processes involve only solid-state diffusion. Solid diffusion is slow with diffusion coefficient $D_s = 1\,E-10$ to $1\,E-20$. Even for the same processing or diffusion time t, which these processes do not have, the diffusion length is only 3.2 microns to 3.2 A, or several orders of magnitude shorter than that in my liquid diffusion case. The mismatch stress gradient is thus proportionately steeper.

Liquid diffusion for 20 minutes thus produces a stabilizing effect or, in the electrical art, pre-aging or burning-in result, that would require about 19 years for solid diffusion results even at moderately high temperatures such as 500° C. Liquid diffusion even for only 3 or 5 minutes still provides a liquid diffusion length of 0.42 or 0.55 mm, which is sufficient for most cases because this length is still several orders of magnitude greater than the above solid diffusion length.

Plasma spraying does involve liquid droplets in rapid transit. These extremely high-temperature droplets impact the substrate at very high velocities resulting in splat cooling with millisecond liquid dwell times. The resultant diffusion length is thus also over three orders of magnitude shorter than my metallizing or metallizing-brazing case. Splat cooling gives very fine grains with high Elastic moduli which actually increase the mismatch stresses. The extreme mismatch stress gradient (stress divided by diffusion length) makes the ceramic-metal bonds fragile. Also, the superheated liquid particles form refractory oxides, nitrides, or other surface layers during transit preventing perfect bonding between the particles themselves. Laser, electron, and some other energetic beam enhanced coating processes also give splat cooling and solid-diffusion conditions.

Without applying any external pressure to force the joining members together, I have used metallizing and bonding processes described above to join various ceramics to metals with pure copper brazes. A typical metallizing process comprises using a mixture of metallizing composition such as $WO_3$—$Fe_2O_3$ or $MoO_2$—$MnO_2$ in suspension or paste form and applied onto the ceramic, heating for 5 to 25 (preferably about 10) minutes the coated ceramic to about 800–1500° C. (preferably 900–1,200° C. in many cases), with no need for the pressure application. The ratio of heavy metal W or Mo to Fe or Mn after reduction from the compounds is generally between 9:1 to 6:4. This metallizing may be followed by or simultaneously done with brazing with, e.g., copper or its alloys. A neutral or reducing atmosphere, such as hydrogen or forming gases of 10 to 40 volume % of hydrogen and 90 to 60 volume % of nitrogen, is the desirable metallizing atmosphere.

The high metallizing temperature ensures thermochemical stability, reliability, and long life of the ceramic-metal bonds.

Different compositions other than the usual W—Fe or Mo—Mn may also be used. For example, metal powders or oxides, carbonates, nitrates, chlorides, fluorides, iodides, bromides, or other compounds of W, Mo, Cu, Ag, Au, Ni, Bi, Sn, Pb, Sb, In, . . . may be employed, generally in amounts from 10–90 by weight percent of the equivalent refractory W or Mo metal.

Even W or Mo is not always necessary if active metals such as Ti and Zr are used to bond the ceramics. But the many other inventions of this application still apply such as on reducing dynamic mismatch stresses, sealing ceramic surface defects, toughening and strengthening ceramic surface regions through microcomposite forming (with hard reinforcing particulates, roots, branches, networks), functional grading, lateral grading, large-area joining, eutectic joining, and the like.

W or Mo may not be necessary for another reason. In joining carbon (graphite, diamond) to iron alloys (steels, stainless steels, alloy steels), a single-step eutectic metallizing/brazing method may be used. This involves contacting carbon directly onto the steel, and heating the assembly to a temperature of from 1080°–1350° C. Pure iron and carbon form a eutectic at 1154° C. at 4.3% by weight. of carbon. But common steels contains other elements such as Mn, Si, S, P, Al, Cr, Ni, . . . . All these elements lower the eutectic temperature and shift the eutectic carbon composition. Many of these elements themselves are eutectic formers with carbon. Hence, useful bonding with common carbon steels occur even at about 1050° C. However, the higher the bonding temperature, the better the bond strength and thermal shock resistance. The controlled cooling method of FIG. 6 may be used in addition here to advantage.

Iron-carbon eutectic is an intermetallic compound. According to Amer. Soc. of Metals' Binary Alloy Phase Diagram, T. B. Massalski, Editor, 1990, p.1182, this eutectic is composed of iron carbide (compound) $Fe_3C$ and iron. Similarly, C and Ti form TiC and $Ti_2C$. Other metals such as those listed above also form carbides. The intermetallic compounds formed in ternary systems such as C—Ti—Pt, C—Ti—Au, Ti—Pt-Au, Ti—Pt—Cu, . . . are even more complex.

The graphite, carbon, or diamond surface may be first coated with a layer of the W/Mo-based material prior to the single,step metallizing/bonding process. The bonded carbon-steel joint may be air or water quenched while hot or molten to achieve the high strength and hardness of steel.

Using the same C—Fe eutectic brazing principle, other carbon-metal bonding methods are possible, according to T. B. Massalski's Binary Alloy Phase Diagrams, ASM, 1986, carbon also forms eutectics with: Au:3/1050 (namely, Au with 3 weight percent of carbon forms eutectic at 1050° C.), B:1.5/2075, Co:2.68/1321, Cr:3.2/1400, Hf:0.2/2250, Ir:1.6/2296, La:2.2/806, Li:2/165, Mn:1.3/1215, Mo:3/2205, Nb:7.5/2339, Ni:0.6/1326, Os:1.32/2732, Pd:2.8/1504, Pt:1.2/1705, Re:1.3/2486, Rh:2.1/1694, Ru:1.8/1924, Si:0.5/1404, Ta:2/2825, Th:0.5/1720, Ti:0.5/1648, U:0.1/1119, V:4/1650, W:1.9/2715, and Zr:0.4/1823. Ternary-eutectics with multiple eutectic or carbide-forming elements selected from the above list are also possible.

The metallizing temperatures and times depend on other factors, such as unwanted reactions. For example, in graphite-aluminum composites, the treatment temperature should not exceed about 750° C., to prevent carbide formations. A carburizing atmosphere, such as one containing $CH_4$ or propane, may be useful to prevent too much loss of carbon in the joining of carbon, diamond, or carbon-carbon composite. Diamond metallizing time may be only one minute to minimize graphitization at high temperatures.

The ceramic I have already bonded with my W/Mo-based metallizing methods described here include: diamond, alumina, zirconia, silicon carbide, beryllia, yttria, graphite, quartz, silicon, mullite, cordierite, Corning's MACOR and Vision glass, piezoelectric ceramics, graphite-aluminum composites, carbon-carbon composites, and 123 high-temperature superconductors. Useful structural metals for the joints include copper, nickel, stainless steel, high-nickel or cobalt iron alloys, or even highly "mismatched" ordinary cold-rolled SAE 1010 carbon steel. Even with the "mismatch" between ceramic and carbon steel, structural joints brazed with pure copper can be repeatedly thermal cycled without fractures between 980° C. (i.e., about 100° C. below the melting point of copper braze) and ice water followed by mechanical shocks including 8 to 10-foot drop tests onto carpeted, wood, or even marble floors.

Similarly, Poco graphite AXF-5Q to SAE 1010 carbon steel rods, $\frac{1}{4}''$ in diameters and joined end-to-end, are almost mechanically indestructible, even when pounded hard with a 12-oz hammer. These joints also are resistant to rapid quench from 800° C. to 0° C. in ice water and severe mechanical shocks. Carbon-carbon composite with carbon steel joints yield comparable results. Joints of diamond to carbon steel can also withstand 850° C. shocks.

These results show that: 1) with my improved processes, low-cost "mismatched" ceramic/metal, carbon-metal, ceramic-ceramic, or ceramic-graphite joints, i.e., the ceramic and metal members are mismatched, or have coefficients of thermal expansion differing by over 40–100%, can be made; 2) these joints can be mechanically strong and thermally shock resistant; 3) the bonding processes, being ceramic material-limited, need no further improvement for the particular material combinations and thermal shock requirements; and 4) these joints are, after bonding and thermomechanical shocks, free of pores, microcracks, inclusions, inhomogeneities, i.e., single metallurgical phase, and other defects at which fractures originate. Each of these shocks would multiply the number of defects exponentially and have failed the joints. These joints, including particularly the metallized layers, thus compare favorably with, e.g., certain ceramic-metal joints or ceramic materials developed at great cost, as reported in the literature.

Surface plating or coating my metal-ceramic joints in various forms with ceramics (including diamond, SiC, $Al_2O_3$, $ZrO_2$) or precious and refractory metals (Pt, Pd, Ir, Hf, Au, Cr,. . . ) makes the joints resistant to corrosion, erosion, oxidation, or surface reactions. Metal-plated or coated ceramic-coated metals, metal-coated ceramics, structural metal-ceramic joints, are biocompatible as implanted bones, teeth, or organs.

Note that our new joints may use only thin layers, not bulks, of tungsten/molybdenum; and generally contain no other strategic and expensive metals such as nickel, cobalt, or chromium. The metallized layer adherently joins to the ceramic. Upon this metallized layer, tenacious, protective metal or ceramic layers can be brazed or formed which resist spalling, peeling, and thermomechanical shocks. Improved corrosion, wear, or frictional properties on these coatings are also possible by suitable selection of the coating materials.

A solid lubricant system may be made, e.g., comprising graphite, talc, or $MoS_2$ powders chemically bonded in copper, bronze, nickel, steel, or cast iron. Also, carbon-carbon composites with improved strength and oxidation resistance are possible. Advanced chemically bonded intermetallic compounds and materials (titanium or hafnium carbide, and titanium or nickel aluminides) are also made available. The same W/Mo-based metallizing compositions are even useful as almost universal high-temperature adhesives or sealants for ceramics or metals.

Ceramic coatings on metal or ceramic-metal bonds can be made even with the metallizing molybdenum and/or tungsten alone without any braze metal layer. The useful operating temperature of the resultant products is then very high, because it is limited now by the melting point of the refractory metallized layer.

The flawless and defect-free quality of my ceramic-metal joints or metallized layers on ceramics, metals, or graphite, or metal-ceramic joints are particularly important for tough, fatigue-resistant, protective, easily wettable, and thermochemically stable coatings on ceramics, metals, graphite, or metal-ceramic joints. A metallized or coated graphite fiber, for example, cannot tolerate a single pinhole or microcrack that allows oxygen to penetrate and to destroy the fiber. Ceramic coatings on metals also cannot have defects when exposed to chemically reactive, high-intensity ion or plasma, high temperature, or other extreme environments. High-melting precious metals such as Pt, Os, and Pd and oxidation resistant metals such as Cr, Al, and Ni are therefore beneficially applied onto the metallized layer, or be formed simultaneously with a metallizing-brazing composition in a single-step metallizing-coating process. Less protective metals such as gold, copper, magnesium, titanium, or zirconium may also be applied onto, formed simultaneously with, the metallizing layer, followed by coating by electrolytic, electroless, or spraying methods, of the above-mentioned oxidation resistant metals for oxidation protection.

In addition, the metallized or metallized/brazed layers have good wetting characteristics. Further, the metallizing or metallized/brazed layer penetrates and seals all surface pinholes, microcracks, or other defects in the ceramic at the interfacial bonding region. These defects are thus converted from crack-initiating points, surfaces, or regions actually into strengtheners. A thick (over 100 microns thick) metal layer of controlled residual stress applying compression to the ceramic further toughens the brittle ceramic. Graphite or carbon fibers or particles may thus not only be oxidation resistant but surface toughened and non-brittle.

My invention also leads to a new generation of "high-fidelity" machining tools made of diamond, alumina, zirconia, boron carbide, BN, SiC, $Si_3N_4$, zirconium carbide, $TiB_2$ (melting point 2900° C., and TiC (melting point 3146° C.), zirconium carbide, or other hard ceramics. With my method, these ceramics are defect-free and tenaciously joined to rigid metals including inexpensive carbon, stainless, tool, or other alloy steels, or even tungsten carbide. In present clamped-on or screwed-on ceramic tool bits, the fragile ceramic is highly prestressed even when the tool is not in use. Maximum useful stresses can, therefore, not be applied during actual usage. My new tools are not prestressed locally and will not work loose under any conditions. Also, in contrast to other bonded ceramic tools, the bonding regions in my new tools are defect-free and actually strengthen the diamond or ceramic, because of sealing of surface defects on the ceramic and compressive surface stresses due to the more shrinking metallized metal layer. The metallize/braze perfectly wets and bonds the ceramic even on the microscopic scale, fully microsupports the ceramic tool tip, and prevents the ceramic from moving, deforming, vibrating, and fracturing. Hence, even under extreme vibrations, heavy loads, or thermomechanical shocks, the machining forces, positions, and motion are transmitted directly and with high fidelity to the very tool tips. Greater machining accuracy, less tool chatter, wear and breakage, and longer tool life and reliability are possible.

Natural or synthetic diamond is rigid, noncontaminating, and chemically stable, readily cut to precise sizes, and easily cleaved and polished to microinch finishes. Excelling also in electrically insulating and thermally conducting properties, it thus is a potential heat-sinking substrate for high-power, laser, microwave, and fast-switching VLSI circuits. These things combined lead to the densest packing, best high power, high frequency, high temperature, and radiation-hard devices. When developed, diamond circuits could operate at up to 600° C. or 475° C. higher than Si or GaAs, respectively.

A most common method of metallization in semiconductor contacting, or for bonding diamond to copper for diamond heat sink application, consists of first sputtering a layer of 600 A titanium, followed by 1,200 A of platinum and one micron of gold. The titanium bonds to the diamond, while the gold bonds to the metal. The platinum is a diffusion barrier to prevent interaction between titanium and gold. The preparation of a diamond heat sink for electronic circuits requires four Ti—Pt—Au—bonding processing steps for bonding top or bottom surfaces of the diamond. The entire bonding process, requiring eight critical processing steps, is thus costly, complicated, and degrading to the product. Still, the product often fails because of peeling, blistering, intermetallic formation, and unwanted reaction between different phases.

In addition, the abruptly graded and multiple serially bonded (Cu—Au—Pt—Ti) layers suffer seriously in two respects because:
1) The mechanically, chemically, and thermally (particularly for diamond heat sinks) weakest layer, no matter how thin, controls the entire bond—Law of the Chain, namely, the strength of a chain is determined by its weakest link; and
2) During any processing or service, the possible existence of severe mismatch stresses between different layers or a single weak, brittle, or unstable phase in the entire relevant phase diagrams at any temperature, no matter how transient, can totally destroy the entire joint—Murphy's Law, namely, any slightest possibility of failure in a system is often the cause of the system failure.

The conventional method for bonding diamond heat sink to bottom metal substrate or to the top electronic circuit involves Ti—Pt—Au multiple layers. According to Amer. Soc. of Metals' Binary Alloy Phase Diagram, T. B. Massalski, Editor, 1990, p.1182, Au and Ti form four intermetallic compounds: $Ti_3Au$, $TiAu$, $TiAu_2$, and $TiAu_4$. Similarly, C and Ti form TiC and $Ti_2C$; while Pt and Ti form $Ti_3Pt$, $TiPt$, $Ti_3Pt_5$, $TiPt_3$, and $TiPt_8$. These intermetallics have high thermal and electrical resistivities, are weak and brittle, and often differ in thermal expansion coefficients compared to diamond or C. The formation of these intermetallic compounds provide many opportunities for the above laws of the Chain and Murphy to operate adversely. Yet, the intermetallic compounds formed in ternary systems such as C—Ti—Pt, C—Ti—Au, Ti—Pt—Au, Ti—Pt—Cu, ... are even more complex, and mostly unknown or predictable.

Thus, the many complex and costly Ti—Pt—Au—bonding processing steps present formidable challenges that have so far failed all materials scientists worldwide. Thermochemical instability may render the Ti—Pt—Au—Cu system unreliable. The National Materials Advisory Board concluded in 1990 that metallization will be "the predominant failure mechanism" in future diamond electronics. See attached copy of the relevant portion of the DTIC Report AdA222,986, p. 81. According to Laser Focus World, Vol. 29, p. 50, 1993, the Japanese engineers in the Ministry of International Trade and Industry (MITI) and the Japan Fine Ceramic Association have also indicated the need for research in diamond bonding and film making for making new diamond-based products. Since diamond film making involves bonding the diamond both to diamond itself and to the substrate, the difficulty of the common Ti—Pt—Au bonding method for diamond is thus evident.

My laterally graded seals, or graded metal-ceramic microjoints in parallel, do not have these two problems. See U.S. Pat. No. 4,890,783. Here, I can use a modified W/Mo-based metallizing process to bond diamond to copper. $MoO_3$ powders are used, together with CuO to supply the braze metal. A low-melting metal such as Sn, Zn, Pb, In, Sb, and Bi is also used to lower the melting point of the braze in the bonding area to keep the substrate metal intact. As an example, with my $MoO_3-CuO-Bi_2O_3$ (volume percentages typically of 60:30:10) of metallizing process at about 1,000° C. for about 10 minutes, I have produced, without any substantive or even any use of Ni, Co, or Cr, a tough, tenacious metallized layer on both the top and bottom diamond surfaces in a simple, reliable, low-cost single-step metallizing/brazing method. In addition, the bottom metallized surface can be bonded to the copper substrate and electrical and thermal contacts can be formed on selected side surfaces of the diamond, all in the same single processing step. The metallizing/brazing liquid produced in this diamond bonding method microscopically perfects the diamond and seals crack-initiating surface defects, replacing surface voids and cracks with solid, thermally highly conducting copper. This bonding method also produces a single-phase, dead-soft annealed copper braze bonding region extending all the way from the diamond to the metal substrate. There are no microscopic or macroscopic pores, voids, microcracks, and second-phase materials in the interfacial bonding regions. The eutectic or carbide-forming method of bonding carbon-based ceramics including diamond with single element Fe, Si, W, and Mo may also be used, as previously described. Instead of heat-sinking copper as the substrate, other substrate materials are equally useful, including Ag, Au, Pt, Ni, silicon nitride, silicon carbide, aluminum nitride, graphite, thermally conductive composites, and berrylia.

The copper braze, produced at near the melting point of copper, is thermochemically highly stable, and electrically fully aged and burned in. It has exceptional temperature resistance (850° C.), has low electrical resistance (no more than 150% of that of pure copper) and absorbs the mismatch stresses for stabilized carrier mobilities in the semiconductor chips. The electrical characteristics of the electronic circuit is thus highly stable and predictable.

The electrical resistivity of Cu, Ag, Au, Pt, and Ti at 20° C. are: 1.67, 1.59, 2.35, 10.6, and 42 microohm-cm, respectively. The thermal conductivity of Cu, Ag, Au, Pt, and Ti at the same temperature are: 0.941, 1.0, 0.71, 0.165, and 0.04 cal/sq cm/cm/°C./sec, respectively. The Young's modulus of Cu, Ag, Au, Pt, and Ti are: 16, 11, 11.6, 21.3, and 16.8 million psi/sq in, respectively. The single-phase high-conductivity braze metals, such as Cu, Ag, and Au, used in my diamond-metal bonds gives high thermal and electrical conductance of the new diamond heat sinks. The thermal or electrical resistivity is no more than 200% that of the pure braze metal Cu, Ag, or Au. The Young's modulus of the dead-soft braze is also no more than 200% of the pure braze metal to provide the critical stress relief means for these diamond-metal bonds. The Young's modulus of the melt-refrozen, dead-soft braze metals such as Cu, Ag, and Au are low, no more than 140% that of the respective pure braze metal, compared favorably relative to the sputtered, high-velocity cold-worked Ti, Pt, and Au particulate layers normally used in bonding diamond, SiC, and other ceramics.

I have noticed the remarkable diamond-copper bond strength by observing that in preparing for microsections, cutting even a 1.5-mm diamond grain represents great difficulties. It generally requires three diamond cutting wheels rotating at 2,000 rpm for three days. Thus, instead of the diamond wheels cutting the small brazed-on diamond grain, this diamond grain is actually cutting the millions of bonded diamond powders on the wheels, while sustaining 8.6 million severe mechanical shocks. My bonded diamond grains thus form excellent machining tools for cutting, milling, grinding, polishing,. . . .

Replacing the Cu and CuO by Ag and AgO, respectively, in the metallizing/brazing composition and reducing the processing temperature by about 120° C. for the lower-melting silver, diamond heat sinks have also been made on silver substrates. Silver is the best metallic conductor, both electrically and thermally. For high-temperature oxidation resistance, the Cu and CuO can be replaced by Au and gold chloride, respectively, with a slightly lower (20° C.) metallizing temperature. Also, the metallized diamond can be braze-bonded to Pt, Pd, and other precious metals, if needed. W and $WO_3$ or mixed W/Mo and $WO_3/MoO_3$, respectively, may be similarly employed. Similarly, the substrate metal can also be Pt, Pd, Au, Ag, or even BaO, AlN, graphite, and thermally conductive composites. Diamond can be brazed onto these thermally conductive substrates if it has a metallized bottom surface.

My diamond heat sinks have thermodynamically stable material systems and can safely be used above 630° C. They dissipate heat vertically by heat sinking and sidewise by heat spreading in the diamond as well as into a sidewise metallized metal layer, or even into a neighboring conductive body on the other side of the side metallized layer. This neighboring conductive body may be metal, diamond, or conductive ceramic. Because of the excellent wetting, there is no air gap or pores between the diamond and the metallized layer and between the metallized layer and the conductive body. In particular, no insulative air layer exist between the diamond and neighboring body. This neighboring body may have a height at least 0.5 or 1 mm higher than that of the diamond, which must be relatively small in size because of its cost. In this case, the sidewise metallized layer intentionally extends substantially above the top surface of the metallized diamond body so that the heat spreading outward from the diamond has a component in a sidewisely upward direction. Note that there must no air gaps because these gaps destroys the lateral heat spreading.

The neighboring conductive body may be another diamond body. This Second body is also perfectly metallurgically bonded onto the same material substrate. The side metallized bonding layers on the adjacent side surfaces of the two diamond bodies then combine into a single integral bonding layer. This can be achieved in the same single-step metallizing/brazing operation by applying the same metallizing/brazing composition on the adjacent surfaces. Upon heating to a high metallizing temperature, these two bodies can be joined together by one single-phase braze material of relatively pure braze metal, even without any application of external force to push them together during the bonding process.

Preferably, the common side metallized bonding layer is no more than about five mils (0.125 mm) thick to maximize the lateral heat spreading from one diamond body to the other. The top and side metallized bonding layers on the two diamond bodies may all terminate to have a common coplanar top surface to facilitate the mounting thereon of a fragile semiconductor or superconductor chip or integrated circuit. In this case, the bottom area of the circuit chip is greater than the top area of either diamond body but smaller than the combined top areas of both diamond bodies. Similarly, a larger number of diamond bodies can be joined together to have a common planar top surface for an integrated planar diamond heat sink, to be used for mounting a much larger and high-power, high-density, high-frequency chip than a single diamond body can accommodate.

It has been proposed to make electronic diamond circuits or heat sinks by thin film methods. The most advanced method is to use a laser synthesis method to produce single-crystal, epitaxial diamond films on copper substrates. See, Narayan et al's article in the Apr. 19, 1991 Science magazine, pp. 416–418 (Copy enclosed). However, since these films are thin (500 Å), only two or three microns in each perfect area, and still imperfect (with severe transient stresses causing periodic parallel microcracks 9 microns apart (in FIG. 2b of the article), useful diamond heat sinks may be difficult to achieve for practical circuits, which are over tens of microns in size. Since in diamond heat sinks lateral heat spreading is far more important than heat sinking, and since the periodic parallel microcracks form vertical insulating walls and destroy heat spreading, no diamond film is actually better than any diamond film since this film always has its own resistance in addition to the associated high resistances of the various Ti, Pt, Au bonding layers.

My laterally graded seals, or graded metal-ceramic microjoints in parallel, as described in U.S. Pat. No. 4,890,783, provides a new solder preform for mounting semiconductor or superconductor chips on the diamond heat sinks. Note that the central region of the preforms has the purer, softer, and more conductive metal than the peripheral regions. This new preform thus usefully manages the thermal dissipation, mismatch stress, and circuit stability. The new diamond heat sink and this new preform also forms a two-stage heat sinking system.

Diamond has the highest thermal conductivity, breakdown voltage, saturated velocity, and radiation resistance but lowest permitivity. Combined, these parameters yield the Johnson figure of merit for the power and frequency performance, and the Keyes figure of merit for the speed, of a transistor manufactured from diamond. These figures of merit are respectively 8,206 and 32.3 times higher for diamond than they are for silicon. High-density, diamond active circuits if perfected can operate at up to 600° C. or 475° C. higher than Si or GaAs, respectively, eliminating cooling equipment now occupying, e.g., much volume of the average satellite.

However, serious material and processing problems still exist. Presently, only p-type conductivity can be obtained at useful current level by implanting boron. The evidence of n-type conductivity is not convincing. Further, even at 1,450° C., it is difficult to completely anneal the heavily damaged regions of the diamond. Most of the n-type conductivity was lost after prolonged annealing. The results of ion implantation are further complicated by the fact that the radiation damage introduces donors and acceptors in equal concentrations. The only n-type diamond samples to date were made by ion implantation of lithium into natural diamond.

Because of the many difficulties of n-type doping by ion implantation, I use a diffusion procedure. Essential to controllable, uniform diffusion doping is the high processing temperature, intimate microscopic contact of the doping source to diamond, and formation of possible diamond-metal doped eutectics which are molten at the processing temperature (See graphite-metal bonding in this specification). That is, a perfect wetting of the diamond with a liquid diffusion source obtains rather than the conventional low-temperature, imperfect contacting, and solid diffusion source in most conventional unsuccessful trials.

Thus, I have solved the unreliable diamond wetting and bonding problems by using a modified W/Mo-based fusion metallizing method. In this diamond bonding method, I use a metallizing/brazing/contacting method consisting of 10–30 v/o (volume percent) Mo, 40–80 v/o Cu and 5–30 v/o Bi for processing at 900°–1170° C. This diamond-bonding method is also useful for other ceramics such as SiC.

My method also solves the problems of low solubility of potential atomic dopants in diamond. This method is extremely simple, and provides ideal conditions for controlled diffusion in diamond. The method achieves many purposes some of which are relevant to dopant diffusion in diamond:

1) Atomically cleans the diamond surface;
2) Perfectly wets the diamond even on the microscopic scale;
3) Defect-freely bonds the diamond upon cooling;
4) Seals porosities, microcracks, and other defects in the diamond surface region, and thereby increases the contact surfaces (for, e.g., improved mass and thermal diffusion) and toughens and strengthens the diamond;
5) Due to the high processing temperature, provides dead-soft shock-absorbing metal layer on the surface, minimizing thermomechanical stresses on, and stabilizing carrier mobilities in, the diamond; and
6) Supplies low-resistance electrical and thermal contacts to the diamond; and 7) Preages and burns-in the metallization contacts, which, according to the DTIC report mentioned above, will be the predominant failure mechanism of hard semiconductors (SIC, diamond).

I use the same fusion metallize/braze medium for n-type doping in diamond, by simply adding n-type dopants in the W/Mo-based metallizing/brazing medium.

Liquid diffusion is rapid, with constant diffusion coefficient $D_l = 1.E-4$ to $1.E-5$ cm$^2$/sec, simplifying doping process control. Processing for our typical 20 minutes gives a diffusion length of up to the square root of $D_l \times t$, i.e., 0.35 to 0.11 cm, amply large for practically all semiconductor device designs. Diffused interfacial regions of graded compositions, microstructures, and mechanical properties also form which are not only highly stress-absorbing but stabilizing to electronic carrier mobilities.

Indeed, my diamond metallizing processing steps fully stabilizes, preages, and burns-in the diamond and, therefore, generates very reliable metallization contacts. Reliable contacts is important because metallization has been considered to be the predominant failure mechanism of reliable diamond electronics. There will also be no dopant outdiffusion and redistribution, because of the thermodynamic equilibrium of constituents even at the high metallizing/doping temperatures. This is in sharp contrast to ion implantation and other doping methods, where the dopant atoms are barbarously forced into the semiconductor with high voltage and momentum, with highly unstable results even at low temperatures.

Most conventional doping processes contain only solid-state diffusion, with diffusion coefficients $D_s = 1.E-10$ to $1.E-20$ cm$^2$/sec, 5–16 orders of magnitude smaller than liquid diffusion. For the same processing time, the solid diffusion length of only 3.2 microns to 0.32 A is several orders of magnitude shorter than our liquid diffusion case and insufficient for device making.

Also, because diamond has very high melting point, the ratio of the conventional diffusion temperature to absolute melting point of diamond is very low. The solid diffusion coefficient must be near the lower end, possibly even below. The diffusion is therefore sub-Angstrom and generally unmeasurable. My metallizing/brazing/diffusion process for 10 or 20 minutes would require tens or hundreds of years of solid diffusion at the usually used "low" diffusion temperatures to achieve the same diffusion results. Comparatively, then, I have a very fast diffusion source.

Hence, I employ the usual N-type dopants, i.e., elements in the Fifth Group of the Periodic Table such as N, P, As, Sb, Bi, V, Cb, Ta, Pa; elements in the Sixth Group (O, S, Se, Te, Po, Cr, Mo, W, U; and possibly elements in the Seventh Group (F, Cl, Br, I, At, Mn, Tc. Not only metals such as As, Sb, Bi, W, Mo, . . ., but oxide, nitrides, phosphides, sulfides, phosphates, fluorides, arsenide, arsenates, . . . are useful as N-type dopants in my modified W/Mo-based, combined metallizing/brazing/contacting/doping process. My W/Mo-based process already contains such N-type dopants as W, Mo, and oxides.

To make the doping more effective, multi-doping techniques are used. That is, e.g., oxides of copper, antimony, phosphorous, arsenic fluoride, bismuth phosphates, . . . are used, in combination, as both the braze and multiple dopants. There are other possibilities. Oxygen and nitrogen, for example, form compounds, eutectics, or other phases with many metals and the potential dopants. The potential doping possibilities further explode. The Cu—O phase stability diagram shows that at a given temperature, the partial pressure of oxygen and solubility of oxygen in copper is very low even at our metallizing temperatures. But $Cu_2O$ has much higher partial pressures and apparent source solubility. CuO has even higher solubility, in fact, five orders of magnitude higher at our metallizing temperature. Copper is a key ingredient in our metallize/braze composition. If it is a strong P-type dopant. I can replace it with, e.g., Sb, or As.

I achieve control of the wettability, dopant source concentration, and the properties of diffusion region and metallized interfacial region, as to, e.g., their thicknesses, effectiveness, and properties, by regulating the metallizing compositions, temperatures, and times. Lower metallizing temperatures, higher melting points of the compositions, or shorter processing times give less doping effects and thinner and less diffused interfacial region, and vice versa.

My new method greatly simplifies the diamond bonding method because it: 1) achieves high-temperature thermodynamic equilibrium of component materials, 2) transforms diamond defects into reinforcements, and 3) minimizes static and dynamic mismatch stresses, yielding a vastly superior product.

This proven simplified processing technique combines the metallizing, brazing, contacting, and high-temperature pre-aging or burning-in steps into one operation. The pre-aged or burned-in connections overcome the predominant failure mechanism in diamond electronics due to improper metallization. For diamond active semiconductors, or diamond heat sink applications in electronic circuits, the microscopically perfect wetting and bonding of diamond by metal maximizes contact area, thermal conductivity, and conductance. The single-phase low-modulus or dead-soft annealed braze absorbs mismatch stresses and strains, assuring high thermomechanical shock resistance and uniform, stable carrier mobilities and predictable circuit characteristics.

Other applications of my specially bonded diamond are as follows: High performance missile domes and optical components require ultrahard materials such as sapphire, spinel, or diamond. Such materials are presently fabricated using diamond abrasive grinding and polishing. This process is slow and very expensive and results in substrate subsurface damage, which directly limits optical and rain erosion performance. Extreme chemical, mechanical, thermal, and electronic stability is thus assured.

In the conventional diamond grinding and polishing wheels, the diamond abrasives are not perfectly or defect-freely bonded, as shown above. The defective bonding, as well as defects in the diamond itself, allows the diamond grains to move, deform, vibrate, and fracture erratically and creates random, unwanted modulations of the signals on the programmed finishing forces, positions, and motions. Hence, the finishing process is out of control. Precision finishing is costly, nonreproducible, and even impossible. Lengthened polishing time, rapid tool wear and vibrations, abrasive grain tear-off, and poor surface finish result.

I therefore make special "high-fidelity" diamond grinding and polishing wheels according to my new diamond bonding technology. The meaning of "high-fidelity" has already been described above. This unique technology produces tenacious, defect-free, thermomechanically shock-resistant, and microscopically perfectly wets and bonds metal layers around the diamond abrasives, eliminating the unwanted modulations of the signals on the programmed finishing forces, positions, and motions.

My diamond metallizing process produces the required diamond abrasive coatings on the new grinding and polishing wheels. The process provides perfectly and rigidly braze bonded diamond abrasives layers onto a hard substrate such as carbon or tool steel, or even tungsten carbide. The metallizing liquid seals all crack-initiating surface defects on the diamond film, provides full, rigid metal microsupport for every diamond grain during the polishing operation, and minimizes induced microscopic bending moments and tensile or shear stresses due to the polishing forces. Hence, even under extreme vibrations, heavy loads, or mechanical shocks, the finishing forces and motions are transmitted directly and with high fidelity to the tips of the macroscopic or microscopic abrasive grains. Greater finishing accuracy, less diamond wear, chatter, and breakage, and longer wheel life and reliability is therefore possible.

This same method can be used to prepare other high-fidelity machining tools such as those for milling, machining, drilling, and the like, or for ultrahard materials other than diamond such as boron nitride, boron carbide, alumina, silicon carbide, .... These ultrahard materials can also be surface finished by grinding and polishing wheels made of a still harder ceramic material including diamond.

Most natural diamond and deposited diamond films still contain many defects such as (111) twins, impurities (nitrogen, nickel, iron, aluminum, and carbon isotopes), porosities, dislocation, stacking faults, grain boundaries, segregated constituents, inclusions, and unwanted phases (such as carbon). All these defects make the diamond film weak, brittle, and sensitive to mechanical vibrations and shocks. Any microcrack, discontinuity, or impurity particle in the diamond film may initiate localized catastrophic failures. These localized failures degrade the product quality, reduce the finishing speed, and cut short the finishing tool life. Hence, all these defects must be sealed, eliminated, or neutralized. This our proposed coating method will do.

The metallizing/brazing liquid seals microscopic crack-initiating surface porosities and other defects, and produces a single, intimately contacting braze structure. These conditions would ensure rigid support to the diamond abrasives during service but minimum mismatch stresses and stress gradients and maximum toughness, adherence, and thermomechanical shock resistance during use. As discussed above, the resultant liquid-diffusion formed metal-ceramic bonds are totally different from those formed by mere compacting, evaporation, sputtering, plasma spraying, chemical vapor deposition (CVD), ... CVD diamond films, e.g., may contain up to 20% porosities. Any porosity degrade the diamond (or other ceramic) heat sinks as to thermal conductivity, strength, toughness, and reliability.

Another application of my diamond bonding process relates to poly-crystalline diamond films. These films are grown by plasma enhanced chemical vapor deposition, which offers a means to protect infra-red window and dome materials in severe environments. The deposited diamond have large grain sizes and random crystal orientations which contributes to reduced optical performance because of scatter. Polishing of the growth surfaces is necessary to reduce the scatter effect. However, the large grains and random orientations makes it difficult to polish these films to high qualities at low cost, particularly on large flat or curved surfaces up to two inches in diameter. My metallizing/brazing method gives microscopically perfectly wetting and bonded metallized layers for diamond and provides a tenacious, defect-free, rigid metal (alloys of Cu, Ni, Fe, ... or even tungsten carbide in cobalt) layer totally embedding all the diamond grains. The metal layer cements together the diamond grains, seals all surface defects, toughens and strengthens the diamond film or layer, firmly microsupports every tiny diamond grains during polishing, and minimizes induced bending moments and tensile or shear stresses on the fragile diamond grains during polishing.

Using the same W/Mo-based method, my diamond-carbon steel bonds have exceptional thermomechanical resistance. Even at high temperatures, there will be no peeling, blistering, unwanted chemical reactions, and new phases, for the reasons given above. The bonds withstood heating to (850° C.) and subsequent cooling to room temperature, without apparent damages. This also indicates, as will be shown, high mechanical shock resistance. Our graphite-carbon steel joints withstood 950° C. in slow cooling but 800° C. in rapid quenching into ice water, contrasting 450° C. for similar joints made at Sandia National Laboratories. In addition, these joints can be almost indestructible mechanically when pounded with 12-oz hammers or heavy objects Our alumina-carbon steel joints withstood 1,000° C. rapid quenching into ice water, while our diamond-copper joints have been tested at 850° C. without failure.

Diamond is transparent to laser. The metallizing/brazing of diamond to metal can be done with pulses of high-intensity $CO_2$ or other laser. The laser beams are transmitted through the diamond without causing much heating, but heat up the metal (steel, Ni, Si, GaAs, ... ) to form joints of precise sizes at exact locations. The bonding can even be done at below the melting point of a low-melting substrate because of the repeated but very localized millisecond or microsecond laser pulses.

Our metal-diamond bonds also have important electronic applications. Of all potential semiconductor materials, diamond has the highest radiation resistance, thermal conductivity, breakdown voltage, saturated electron current, but the lowest dielectric constant. These things combined lead to the best high power, high frequency, high temperature, and radiation-hard devices. Diamond circuits could operate at up to 600° C. or 475° C. higher than Si or GaAs, respectively, eliminating cooling equipment now occupying, e.g., 65% of the average satellite.

Coated with my metallized/brazed films up to 20 microns thick, ceramics, boron, graphite, diamond, or glass powders 0.5 through 50 to 200 microns in diameters, are also suited for specific particulate reinforced composites. Upon compacting and sintering these metal coated particles to proper densities and mechanical properties, special acoustic or otherwise damping materials are obtained.

With my methods, sapphire, quartz, alumina, or zirconia tubes can be sealed vacuum-tightly to niobium, tantalum, or other ceramic tubes to make useful electronic cavity or optical windows for services to or over 1300° C. or 1500° C. My bonding method will also avoid the usual frits seals which are weak, contaminating, short-lived, deteriorating to electrooptical characteristics of the component, and otherwise unreliable in operations.

Defect-free or flawless coatings or bondings are also necessary to contain dangerous materials and should be used to replace weldments which almost always have bubbles, oxides inclusions, segregation patterns, severe residual stresses, weak grain boundaries, or other defects.

The strong, defect-free, and thermomechanically shock-resistant quality of the metallized layers on ceramics, graphite, diamond, and reactive metals such as titanium, zirconium, aluminum, or stainless steel is especially important in the manufacture of advanced composites. Here, the reinforcing fibers, particulates, sheets, or two- or three-dimensional weaves of the ceramics, graphite, boron, oxides of aluminum or zirconium; and carbides or nitrides of Ti, Zr, Hf, V, Nb, Ta, Cr, Mo, or W; borides of carbon or nitrogen; silicides, aluminides, other intermetallics; diamond; and metals are then perfectly not only wetted by, but bonded to, the matrix of metals, ceramics, carbon, borides, nitrides, carbides, diamond, . . . . Good interfacial bond strengths in, e.g., about 20 volume % graphite, SiC, or $Si_3N_4$ fibers or particles in Type 6061 aluminum, alumina, or zirconia, allow load transfer to occur between matrix and reinforcing particulates, fibers, or weaves thereby giving maximum specific moduli and strengths. These defect-free bondings at the interfaces prevent debondings and allow ideal load transfer between, within, and along the reinforcing members thereby achieving maximum strength, production yield, and productivity at minimum costs.

Useful relatively low-melting soft, yieldable braze metals include pure copper (with melting point 1083° C.), silver (961.9° C.), gold (1064.4° C.), tin (232.0° C.), zinc (419.6° C.), lead (327.5° C.), antimony (630.5° C.), cadmium (320.9° C.), aluminum (660.4° C.), magnesium (648.8° C.), gallium (29.8° C.), indium (156.4° C.), thallium (303.5° C.), bismuth (271.3° C.), . . ., and their alloys. Higher-melting metals such as beryllium, chromium, cobalt, hafnium, iridium; iron, manganese, nickel, niobium, osmium; palladium, platinum, protactinium, rhenium, rhodium; ruthenium, samarium, scandium, silicon, tantalum; thorium, titanium, uranium, vanadium, yttrium, zirconium, and their alloys, allow the practical operating temperatures of the joints to be raised to near their respective melting points of 1278, 1857, 1495, 2227, 2410; 1535, 1244, 1455, 2468, 2700; 1554, 1772, 3000, 3180, 1966; 2310, 1300, 1541, 1430, 2996; 1800, 1660, 1130, 1890, 1522, and 1852 degrees Centigrade, respectively.

When molybdenum is used as the metallizing layer together with a braze metal such as osmium, rhenium, platinum, protactinium, rhenium, and tantalum braze layer, the lower-melting molybdenum, i.e., at 2810° C., rather than that of the braze layer, generally limits the useful temperature of the joint. Similarly, when tungsten (melting point 3410° C.) is used as both the metallized and brazed layer for more refractory materials such as carbon-based materials (melting point 3650° C.), the lower melting tungsten dominates as to the practical use temperature of the joint or coating. A variety of new, W/Mo metallized plates, fibers or particulates of, e.g., SiC, $Si_3N_4$, $Al_2O_3$, $ZrO_2$, mullite, cordierite, diamond, glass, quartz, and other ceramics can thus be produced that can be used as reinforcement in composites for temperatures over 1500°, 2000°, 2500°, 3000° C., or higher.

Chemical reactions between the matrix and reinforcement are serious problems in composites. In graphite-aluminum composites, for example, the graphite reinforcement may react with matrix aluminum to form brittle aluminum carbide. At a given service, processing, or other operating temperature over about 800° C., the graphite-aluminum interfacial reactions may thus be intolerable. High-melting metals given above and used as the metallized/brazed layers on the graphite slow down the elemental diffusion rates and, therefore, graphite particulate- or fiber-matrix interfacial reactions. The heavy metals W or Mo and refractory metals slow down even further. This is because the elemental diffusion rates are functions of the ratio of the operating temperature to the absolute melting temperature. At the same operating temperature of, e.g., 550° C., this ratio for aluminum directly contacting graphite is $(550+273.1)/(660.4+273.1)=0.882$. With nickel braze on the graphite fibers according to my invention, the interfacial reaction is now between nickel and graphite, and the same ratio is reduced to $823.1/(1455+273.1)=0.476$. When the graphite fibers are metallized with Mo or W, the same ratios are further reduced to 0.267 or 0.223, respectively. With a wide variety of available metallizing alloys (e.g., W—Fe, Mo-Mn, . . . ) and coated layers on ceramic reinforcing fibers and particulates, these ratios can be selectively chosen to be less than, e.g., 0.6, 0.5, 0.4, 0.3, 0.22, or even less. The matrix-reinforcement interfacial chemical reactions are thereby reduced, weakening of composite strength is minimized and embrittlement of reinforcement or destruction of composite avoided.

Interfacial chemical reactivity between, e.g., ceramic reinforcement and the metal matrix, can be further suppressed or totally eliminated by coating the metallized/brazed layer with chromium or aluminum. Chromium, aluminum, and their alloys form adherent, dense oxides that resist further oxygen penetration to, e.g., the underneath graphite fibers. These specially metallized/coated graphite or carbon fibers are thermochemically stable in oxygen or other oxidizing atmospheres.

Even mismatch ceramic-metal joints made according to my invention refused to fail under repeated, rapid and severe thermomechanical shocks. Further, the final forced fractures occur away from the bonding regions. This shows that the bonds are free of flaws, microcracks, inclusions, and other defects. In addition, the bond is actually stronger than the weaker ceramic member. This is because the liquid layer formed on the ceramic surface during the metallizing step, generally from 5 to 50 microns thick, actually seals surface notches and other flaws. The metallizing W/Mo ingredients, from examination of microphotos, also strengthen the ceramic at the interfacial region through solution strengthening, or formation of microcomposite reinforcement in the form of precipitated particulates and reinforcing roots, branches, or networks.

In many composites, weight is a critical consideration. Because of the heavy densities of W and Mo, a very thin W/Mo-based metallized/brazed layer, down to several atomic layers in thickness, may be used with or without any copper, nickel, or other braze metal. The formation of a surface liquid diffusion layer 3 to 30 atomic layers (about 10 to 100 A) takes only 10E-9 to 10E-7 seconds, if a liquid diffusion coefficient of 10E-5 cm×cm/sec is used. The control of such extremely thin layer can still be achieved by applying a thin layer of the metallizing solution containing the limited but exactly controlled amount of molybdate or tungstate compounds.

Another problem with composites is that ceramic, graphite, and carbon fibers are very difficult to be perfectly wetted by, or bonded to, metals, other ceramics, or even to epoxy. Because of this difficulty, an airplane or other vehicle made of these composites often structurally fails under cyclic environmental heat-moisture conditions. Under capillary attraction forces, rain or condensed moisture on the composite surface deeply penetrates, or is sucked in, along the tiny passageways in the unbonded or poorly bonded interfacial regions between the graphite or other ceramic fibers and the epoxy, metal, or ceramic matrices. This penetration is facilitated by air release in, for example, an improperly oriented one-dimensional reinforcement where water enters from the outside skin and move freely along the entire length of the fibers, with entrapped air being forced to leave out of the inner surfaces. This fills the composite structure with water. When the environment turns cold, the filled water expands on freezing, disruptively enlarging the passageways and further debonding the reinforcement from the matrices. Repeated filling-expanding cycles may destroy the composites. When a high-altitude airplane lands in a hot humid weather, moisture automatically condenses onto the very cold composite skin and similarly fill the passageways. The vehicle may take off again into the same freezing attitude where the filled water expands on freezing with disruptive forces. Multiple cycles of landing and high-altitude flying also destroy the composite.

Figure 2A:
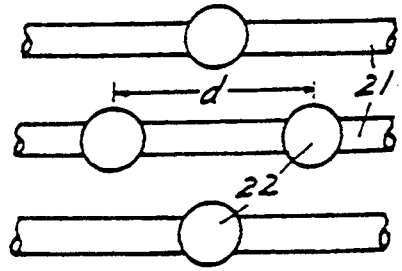
FIGS. 2a–2b show nodular bonding spots on reinforcing carbon fibers in carbon composites.
Figure 2B:
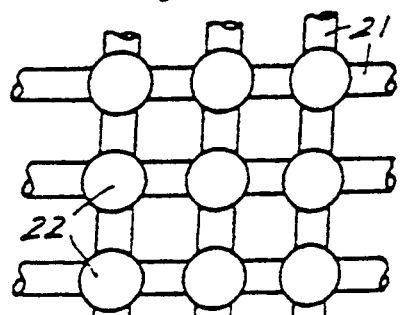

By uniformly covering these fibers with flawless metallized W/Mo-based coatings, with or without brazing materials, the bonding between these coatings and the matrix will also be flawless. Water penetration is then impossible. Periodic coating of all the strands of these fibers 21 along their lengths with nodular metallized spots 22 at a specific distance d apart breaks up the passageways into small compartments of length d (FIG. 2a). Water can now penetrate to no more than the same distance d below the composite surface. Dipping a two-dimensional or three-dimensional fiber weave into a W/Mo-based metallizing solution or paste, again with or without braze, preferentially coats only the intersections of the fibers with the metallizing compound to thereby form the required nodules for stopping deep water penetration (FIG. 2b). The size of the nodular metallized spots can be controlled by adjusting the viscosity and/or solid content of the solution or paste. Wetting control with the addition of acetone, alcohol, house detergent (e.g., Wisk) also helps.

The reinforcing graphite or other ceramic fibers selectively but perfectly bonded at the nodulated or coated spots in the composites achieve excellent load transfer between fibers, or even along the fibers in metal-matrix composites, but allow systematically and controllably unbonded or weakly bonded regions between the nodules, lending to excellent toughness as well as heat and shock resistances.

The ceramic metallizing processes described in this invention also allow the brazing or coating of the internal or external surfaces of ceramics of controlled densities or porosities. More specifically, porous alumina, zirconia, silicon carbide, yttria, mullite, and cordierite have already been metallized with my methods on either the internal pores, external surfaces, or both. Substantially 100% of the internal surfaces of the porous ceramic can be metallized by my processes. Ceramic filters for, for example, molten steel, aluminum, or other metals or materials are already in wide uses. But the difficulty of perfectly bonding these weak and porous filter ceramic medium to each other or to metals make their uses difficult, tricky, unreliable, and often dangerous. By bonding these ceramic filters to steel wires or plates, as I have done, these handling problems are minimized.

Multi-stage ceramic filters of alumina, zirconia, silicon carbide, yttria, mullite, cordierite, glass, or other ceramics strongly bonded to the same or different ceramic of the same or increasingly finer pore sizes can now be joined together, one on top of the other. Metal-reinforced multi-stage filters can also be made for, e.g., added strength through metal strengthening; multiple-purpose separations of gases, liquids, or solids from one another through physical means due to size differences; absorption by carbon; catalytic reactions by platinum; liberation or desorption of gases such as oxygen, nitrogen, carbon oxides, or hydrogen from the bonded oxides, nitrides, carbides; hydride for doping or addition to the molten metals or other materials; separation of substances of the same gas, liquid, or solid phases; and other special features functions.

Ceramic filters for air, gas, oil, transmission fluids, and cooling water on automobiles, diesels, power generating equipment, and other machineries are already available. Similar filters for various other fluids including molten metals such as steel or aluminum, or catalytic reactors can, with my bonding method, be strongly attached to internal or external carbon steel or stainless steel containers, other metallic, carbon, or ceramic hooks, knobs, holders, fasteners, protrusions, strengtheners, friction contacts, or springy devices for easy handling or to form fluid-tight enclosures without fluid by-passings.

Catalytic materials such as platinum alloys may also be coated on the metallized layer via diffusion coating, brazing, electrolytic or electroless plating. Reactive materials such as yttria or CaO can also be made porous by sol gel, or by controlled powder packing and sintering, to achieve any desired powder sizes and packing or sintered densities. Such reactive ceramic filters, properly bonded to metal structures, may be used, for example, to remove weakening sulfur in high-quality tool steel poured through these filters.

An electric heater may surround, or be embedded in, the porous ceramic filter for periodical activation with electric ohmic heating to burn to ashes or gases the materials remaining on the ceramic filtering medium. This achieves reusable or self-cleaning results.

Many other uses in differing industries of my bonding methods are readily seen. These include ceramic composites, graphite composites, intermetallic composites, metal-matrix composites, coatings on ceramics, graphite, or metals, high-strength chemically bonded ceramics, and self-lubricating materials containing, e.g., lubricating talc, $MoS_2$, or graphite particles in iron, steel, copper, or nickel. The composites may involve reinforcing fibers or particulates of ceramics, intermetallics, graphite, or metals in a matrix of ceramic, intermetallic, graphite, or metal.

Using my metallizing methods described above, metallized refractory metallic compounds can be formed for uses as the matrix or reinforcement for composites. These compounds include: oxides of Al, Ba, Be, Ca, Cr, Eu, Gd, La, Mg, Ni, Pu, Ru, Sm, Sc, Si, Th, Ti, U, V, Y, and Zr; carbides of Al, B, Ba, Be, Ca, Hf, Mo, Nb, Si, Ta, Th, Ti, U, V, W, and Zr; borides of Ba, Ca, Ce, Hf, Mo, Ni, Sr, Ta, Th, Ti, U, V, and Zr; Sulfides of Ca, Gd, Sr, U, and Y; nitrides of Al, Hf, La, Nb, Nd, Sc, Si, Pr, Pu, Ta, Th, Ti, U, V, Y, and Zr; and aluminides of Fe, Ni, Pt, Be, and Ti. Particularly attractive among these compounds are: $Si_3N_4$, SiAlON, SiC, $Al_2O_3$, mullite, AlN, $B_4C$, $TiB_2$, and BN.

Light, strong, tough, and reliable structural Al, Mg, Be, Ti alloys in composite forms can thus be made with metallized graphite, SiC, or other ceramic reinforcement that will operate over 480° C.

Powders of a ceramic, carbon, intermetallics, or reactive metal may be similarly metallized to achieve flawless and perfectly wetting surface characteristics so that the sintered powder compacts or liquid metal infiltrated composites will form that have unusually high strengths, densities, and thermal conductivities. Such metallized powders can also be cast as particulate reinforcements or strengtheners. These same powders can be cast (by, e.g., hot squeeze method) to achieve near net shape or net shape into complex structures or components.

Figure 3B:
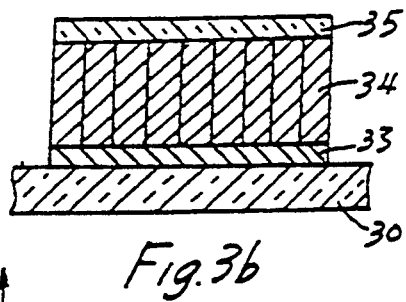
FIGS. 3a–3b show a multi-purpose bonding method for high temperature ceramic superconductors.
Figure 3A:
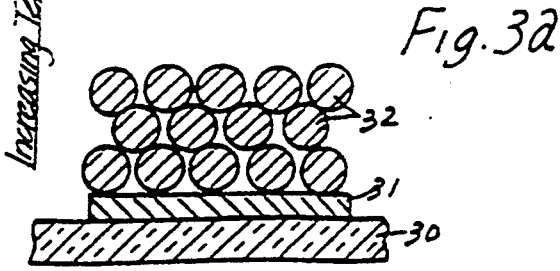

A multi-purpose procedure for bonding, sintering, purifying, densifying, strengthening, and otherwise improving the high temperature 123 ceramic superconductor is shown in FIG. 3. High temperature superconductors are superconductors which superconducts at above 90 degrees K. (Kelvin). In this multi-purpose procedure, a layer of a suitable $MoO_3$-based mixture 31 is formed at selected spots on the copper substrate 30, as shown in FIG. 3a. $MoO_3$ is the key ingredient in many of my Mo-based metallizing operations. It melts at 801° C., but the melting point can be lowered or raised to selectable temperatures by forming eutectics or compounds with, e.g., CuO, BaO, and $Y_2O_3$, and other oxides such as AgO, CaO, or TlO (Thallium oxide), or even flourides, chlorides, or iodides in view of Ovshinsky's promising results on superconducting and particularly current-carrying capabilities. Upon this $MoO_3$-based layer is spread the $YBa_2Cu_3O_{7-x}$ powders 32. A vertical temperature gradient is applied to the composite so that the top of the superconductor powders is at least 20° to 50° C. below its melting point, while the bottom of the $MoO_3$-based layer is above the melting point of this mixture. This mixture layer will then melt, form the liquid-diffused bonding interfacial region 33, and sweep upward (FIG. 3a) to achieve the following highly desirable results:

1. Metallizing and bonding of the bottom layer of 123 superconductor to the copper substrate;
2. Temperature gradient zone-melting to purify the superconductor boundaries according to Pfann (See: Zone Melting, Wiley, 1966);
3. Vertically oriented, upward superconductor columnar grain growth 34;
4. Grain boundary scavenging, oxygenation, or halogen doping;
5. Liquid phase sintering of the superconductor particles for improved sintering speed, density, mechanical strength, and material stabilities partly also due to the purified or doped grain boundaries;
6. High critical current density of the purified, thinner, and oriented grain boundaries;
7. Cushioning or shock-absorbing qualities of the liquid-diffused, chemically and mechanically graded interfacial layer 33 between the superconductor film and substrate; and
8. Simple, low-cost, single-step and mass-producing but potentially high-yielding film-making operation.

After this special temperature-gradient multi-purpose operation, most of the impurities will be dissolved in the sweeping zone. This zone eventually comes up to the surface to be frozen into a highly impure layer 35. This impure layer can be removed by, e.g., grinding or chemical etching with mineral acids. See FIG. 3b.

Low current density in high $T_c$ ceramic superconductors is still a major problem, particularly in polycrystalline, bulk or thick film materials. Improper grain boundaries are mostly responsible. My special multi-purpose bonding method overcomes this problem.

Other high-temperature ceramic superconductors such as $Tl_2Ba_2Ca_2Cu_3O_{10}$ and $TlCa_2Ba_3Cu_4O_x$ can be similarly bonded or treated for properties improvement with the above method. The substrate does not have to be pure copper, but can be other metals such as aluminum, nickel, or iron, glasses, graphite, or diamond. In addition, other ceramics such as $Al_2O_3$, $ZrO_2$, SiC, carbon, glasses, diamond, or even metals powders or filaments, may be similarly bonded onto metallic, ceramic, glass, or carbon substrates.

The ceramic layer 34 with thinned, purified, oriented grain boundaries have improved physicochemical properties including thermal and electrical conductivities since grain boundaries generally contribute to high resistivity.

In ceramic-metal joints other than for superconductor application, however, the above zone-melting procedure is harmful from the bond strength viewpoint. This is because the last-solidifying layer, usually of complex ceramic eutectic compounds, is weak and brittle and reduces the joint strength. The proper cooling direction after the metallizing here should, therefore, not be vertical but horizontal. In this way, the last-forming layer is laterally swept out of the joint region without harmfully affecting the joint strength.

Low current density in high $T_c$ ceramic superconductors is still a major problem, particularly in polycrystalline, bulk or thick film materials. Improper grain boundaries are mostly responsible. My special multi-purpose bonding method overcomes this problem.

According to the above disclosures, I microengineer the ceramic-metal, ceramic-metallizing layer, and/or metallizing-braze layers by substantial thickness and, more important, graded composition, thermoconductivity, and mechanical properties. The W/Mo-based metallized layer may be, for example, 10 to 20 or 30 microns containing a graded interfacial layer up to 5 or 10 microns. The effective liquid diffusion length described above may range from 5 to the entire 30 microns. These layers are obtained by liquid diffusion, generally through melting for over five minutes but up to one hour. The Cu, Ni, or alloy braze layers may also be chemically, mechanical, and physically graded, as described above.

Figure 4A:
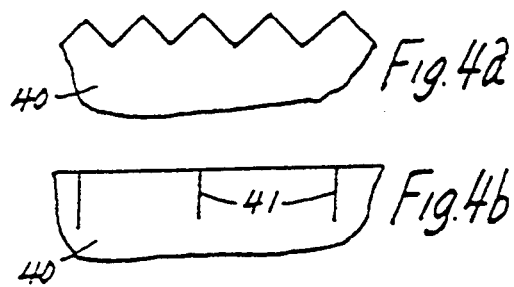
FIGS. 4a–4d show newly microengineered microstructures of the bonding interfacial regions.
Figure 4B:
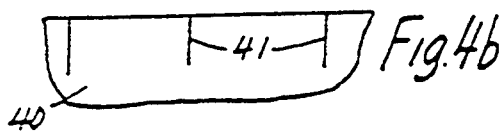
Figure 4C:
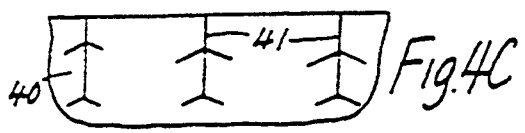
Figure 4D:
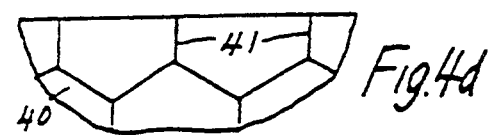

Another important grading of the interfacial layer relates to the microstructure. Many conventional joints rely on superficial adhesion, weak and defective chemical bonding, or mechanical anchoring with roughened surfaces. Rough surfaces increase surface area by about 41.4% with 45-degree slopes or valleys (FIG. 4a). An important feature of my invention is the principle of rooting (FIG. 4b), branching (FIG. 4c), and networking (FIG. 4d). Straight roots of the metallizing materials 41 penetrate, during the metallizing or rapid liquid diffusion period, deep along the ceramic grain boundaries 40 in the ceramic. These roots may be in the form of fibers located at the intersections of the multiple boundaries, or in the form of sheets each located between two adjacent ceramic grains. These fibers and sheets may be straight, extending generally perpendicularly to the ceramic-metal interface (FIG. 4b). They may form branches following the grain boundaries (FIG. 4c). These roots may even flow deeply into the grain boundaries and turn or curve around to form a partial or complete network (FIG. 4d). The formation of these fibers or sheets depend on the surface energies of the metallizing compounds relative to those of the ceramic grains at the metallizing temperature. The depth of penetration also depends on these energies, but primarily on the metallizing temperature and time.

Preferably, these penetrating metallizing materials form reinforcement in a matrix of the ceramic material at the interfacial region. This can be achieved by selecting a W/Mo-based metallizing composition which, with the ceramic at the metallizing temperature, forms hard (Mohr hardness over 8 or 9 versus less than 7 or 6 for the matrix), tough, and strong compounds. Useful compounds include $PbMoO_4$, $MgWO_4$, $CaMoO_4$, $MnWO_4$, $MnMoO_4$ and the like. In practice, I simply use pure starting materials such as $MoO_3$, $WO_3$, PbO, CaO, ..., prepare the exact or near stoichiometric compositions for the metallizing compositions, and metallize at a temperature 50° to 200° C. above the melting points of these compounds. By varying the metallizing time, the grain-boundary reinforcing compounds penetrate to different depths, according to the square root of time diffusion law. For example, for a liquid diffusion case with a diffusion coefficient of 10E-5 cm×cm/sec, metallizing for 5 to 60 minutes gives a diffusion length or penetration depth of about 0.055 to 0.19 cm. The required liquid metallizing times are 30.2 and 361 seconds, respectively, if a liquid diffusion coefficient of $10^{-4}$ $cm^2$/sec is used. If the liquid diffusion coefficient of $10^{-5}$ $cm^2$/sec is chosen, the required metallizing times are 302 and 3,610 seconds, respectively.

I also achieved moderately different penetrations of reinforcing particles, fibers, or sheets of different penetration depths by changing the metallizing compositions, e.g., from the W-based type to the Mo-based type.

Because of the many benefits of my inventions, the ceramic metallized coatings and metal-ceramic bonds are thermally stable and useful at high service or use temperatures, e.g., above 630° C. At these high temperatures, the ceramic coatings or bonds of this invention not only remain solid, but are structurally useful and can carry nominal external loads. Even loads higher than the ceramic's nominal strengths are likely because of the microcomposite and favorable residual stress formations, surface sealing, toughening, and strengthening, and many other techniques described above. By comparison, conventional ceramic coatings contain weak and unstable phases, or become molten, partially molten, or viscous, and cannot, therefore, carry any meaningful external load at high temperatures. The common ceramic-metal joints fail for similar reasons.

The metallized layer has low viscosity, and wets the ceramic with a wetting angle of less than 15° or 5°. Preferably, this angle is close to 0°, perfect or nearly perfect wetting then occurs. This metallizing liquid will wet not only the top surface, but also any surface pores, microcracks, and other defects, transforming these crack-initiating defects into useful reinforcements. In fact, microcomposite bonding region forms, toughening and strengthening the ceramic bonding surface.

As shown in FIGS. 4b–4d, the molten metallized/brazing materials of the metallizing composition not only form the metallized bonding layer to join the ceramic to form bonded ceramic structures, but also penetrate along the ceramic grain boundaries to form two-dimensional or three-dimensional metallic reinforcement in the form of fibers, sheets, branches, particles, roots, or net works. The reinforcement is strengthening to the ceramic if the metallizing/brazing material is relatively hard, such as the various reinforcing compounds of $WO_3$ or $MoO_3$, but toughening is the same materials are ductile such as Cu, Al, Mg, . . . .

The metallic reinforcement fibers, sheets, networks, and branches additionally define the ceramic grains and completely (FIG. 4d) or partially (FIGS. 4b and 4c) separate the ceramic grains. These soft and ductile ceramic grain boundary materials absorb thermomechanical shocks, making the ceramic less brittle. Through yielding and stress absorption, the thermal mismatch stresses and strains are localized within the enclosed ceramic grain, and cannot transmit to neighboring grains, at least not with full force. These metallic reinforcement thus acts as shock absorbers, stress and strain isolators, and ceramic strengtheners or tougheners.

These reinforcing or yielding metallic components in FIG. 4a–4d, 7, and 9a–b further separate or divide a large joining area into compartments so small that the metallic components can restrain or absorbing the mismatch stresses and strains within each compartment. These metallic components also prevent the propagation of these stresses and strains into other compartments, and minimize the build-up of these stresses and strains from the entire large area. This "divide-and-conquer" mechanism thus solves the so-far insolvable problem of thermal mismatch problem in bonded large areas. That is, dissimilar material joints may no longer be limited in size or to CTE match.

The top surfaces of the metallized parts shown in FIGS. 4a–4d have metallized layers whose chemical compositions are the same, or nearly the same, as those of the roots, branches, or networks 41. Since this metal compositions have higher coefficients of thermal expansion than the ceramics 40, mismatch stresses arise on cooling from the high metallizing temperature to room or service temperature. Specifically, the more shrinking, top metal layers will be under tension, compressing and further toughening and strengthening the ceramics 40. Comparable to the distance between two neighboring roots, branches, or network boundaries, the length or depth of the roots or branches may be from 2 to 200 microns, while the networks may even extend deeper. That is, a ceramic surface region from 0 to over 200 microns are thus toughened and strengthened through the compression applied by the more shrinking metal layer on the top surface of the metallized ceramics 40.

Active metals, such as Ti, Zr, Pt, and Nb, and their alloys, with or without other metals such as Ni and Cu, are also useful metallizing materials. But these active metals require pure metals, not oxides, carbonates, . . . . With oxygen, the active metals form stable oxides, which are difficult to bond or metallize. Under non-oxidizing conditions, and at processing temperatures sufficiently (50°–400° C.) above their melting points to decrease their viscosity, these active metals in molten form can also wet easily on most ceramics, have small wetting angles under good vacuum and, therefore, not only metallize and bond, but also penetrate to form roots, branches, and networks, just like my W/Mo-based metallizing compositions. Some of their compounds, such as titanates, zirconates, or other oxygen compounds of these active metals with Ca, Mg, Sr, and Ba, are also very hard and strong (at least 10%, preferably 20% harder in Vicker's hardness and/or stronger in tensile strength than the ceramic), and thus form good reinforcements for the microcomposite bonding regions.

Thus, with my new ceramic-ceramic or ceramic-metal joining methods, new structural joints, coatings, or surfaces can be produced that have wide uses due to their hardnesses (diamond, alumina, zirconia), hardness and resistances to wear (diamond, zirconia) or corrosion (diamond, carbon, alumina), electrical or thermal conductivity/insulation (zirconia, beryllia, diamond, silver, stainless steel), catalytic activity (platinum), and other properties or appearances.

Tool bits of silicon carbide or nitride, alumina, diamond, boron carbide, and other cutting or abrasive materials can, for example, be metallized with my methods and joined to steel holders to form cutting, drilling, milling, or other machining tools. Particles of the same materials, mixed with the W/Mo metallizing compounds together with copper or nickel brazing alloys, can be spread onto inexpensive carbon steel sheets 0.010 to 0.250 inches thick. Upon heating in a reducing atmosphere, a steel sanding sheet or block is formed. The braze metal may be very thin and merely joins the abrasive particles to the steel plate. The same braze metal may have a thickness up to 95% of the size of the particles, to support fully and hold strongly these particles while still allowing their sharp cutting edges to perform.

Figure 5:
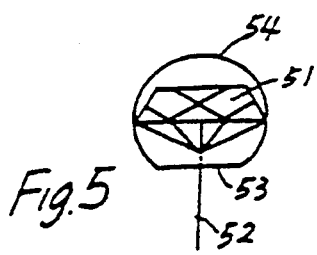
FIG. 5 shows a bonding method for mounting diamond or other gem stones.

Gem stones such as diamond, sapphire, quartz, and the like can be mounted onto metal holders. Because of the excellent strength of the bond, the gem stones need not be constantly prestressed and minimum contact with holding metals is needed. As shown in FIG. 5, diamond 51 can now be mounted on the tip of a fine wire 52 so that practically its entire back surface can be brilliantly illuminated. Also, different back characteristics (color, texture, and reflectivity) can now be instantly changed.

Figure 9A:
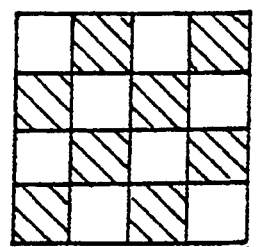
FIGS. 9a–9b show a method of overcoming mismatch stresses on long or large-area coatings or joints.
Figure 9B:
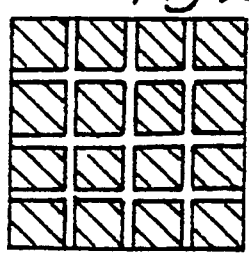

FIG. 9 shows a method of making large size ceramic coatings on another material or ceramic-bonded joints. The principle is to break the large area, or length for a one-dimensional object such as a rod, into many segments so that each segment is of such a small area or length that the mismatch stresses or strains are tolerable by the ceramic. The bonded areas are represented by the white or hatched squares in the chess-board pattern of FIG. 9a. This joint or coating in FIG. 9a is even vacuum-tight because the corners of the many small squares are connected and gas or vacuum-tight. FIG. 9b shows another method of making large ceramic coatings or joints. The bonded areas may be the hatched squares, in which case, one side of the joint or coat is fluid communicable with the other side. Alternately, the bonded areas may be the white grid pattern between the squares left by the hatched squares, in which case the joint or coating is again vacuum, gas, or liquid-tight as in the joint or coating of FIG. 9a.

The invention, as described above, is not to be construed as limited to the particular forms disclosed herein, since these are to be regarded as illustrative rather than restrictive. Various combinations, equivalent substitutions, or other modifications of the preferred embodiments described herein are obviously possible in light of the description, without departing from the spirit of the invention. In particular, other ceramics such as alumina or zirconia may be used instead of MACOR with the same or a modified metallizing composition. Accordingly, the invention is to be limited only as indicated by the scope of the following appended claims:

I claim:

1. A method of making a bonded ceramic structure comprising a ceramic bonded onto a substrate, comprisings selecting the substrate having a top surface;
   supplying the ceramic having a bottom surface;
   positioning the ceramic to have at least a part of its bottom surface in contact with the top surface of the substrate;
   furnishing at the contact area between the ceramic and the substrate a bonding substance containing a carbide-forming metal which chemically reacts with the ceramic, above a first temperature of below 1500° C., to form a metal carbide capable of chemically bonding to both the ceramic and the substrate,
   said carbide-forming metal being selected from the group consisting of Au, B, Fe, Ir, La, Li, Mn, Mo, Os, Re, Rh, Ru, Si, Th, U, V, W, and mixtures or alloys thereof; and
   without applying external pressure in the entire bonding process heating the ceramic in contact with the substrate above the first temperature to cause the chemical reaction to occur thereby forming a first bottom bonding layer microscopically substantially perfectly bonding the top surface of the substrate to the at least a part of the bottom surface of the ceramic;
   the first bottom bonding layer being void-free and microcrack-free and from 100 Angstroms to 0.125 mm thick, and comprising essentially of the metal carbide.

2. A method as in claim 1 wherein the furnishing step comprises furnishing the bonding substance containing the carbide-forming metal which forms the metal carbide capable of directly bonding, without braze, compliant, or other intermediate layer, to both the ceramic and the substrate.

3. A method as in claim 1 wherein the carbide-forming metal consists essentially of a single metal selected from the group consisting of Au, B, Fe, Ir, La, Li, Mn, Mo, Os, Re, Rh, Ru, Si, Th, U, V, and W.

4. A method as in claim 1 wherein the heating step comprises heating the ceramic and the substrate together in a gaseous environment comprising essentially of a gas selected from the group consisting of hydrogen, nitrogen, hydrocarbon gas, and mixtures thereof.

5. A method as in claim 1 wherein the heating step comprises heating to form the metal carbide on the ceramic and to melt at least part of the metal carbide to thereby form a melted and re-solidified, first bottom bonding layer for bonding the ceramic onto the substrate.

6. A method as in claim 5 wherein the ceramic contains in the surface region thereof surface defects; and wherein said furnishing step comprises preparing a wettable metal carbide which is molten above the first temperature;

at least partially melting the wettable metal carbide;

allowing the molten, wettable metal carbide to penetrate into the ceramic surface region particularly relative to the surface defects contained therein thereby sealing at least one of the ceramic surface defects; and solidifying the molten metal carbide to provide a solid strengthener in the ceramic.

7. A method as in claim 4 wherein the furnishing step comprises:

mixing the bonding substance containing the carbide-forming metal, a braze which alloys with the metal, and a temporary binder to provide a coating material; and applying the coating material onto a selected surface of at least one of the top surface of the substrate and the at least a part of the bottom surface of the ceramic; and wherein the heating step comprises heating above the first temperature to initially form a metal carbide coating on the ceramic and thereafter braze the metal carbide-coated ceramic onto the substrate.

8. A method as in claim 7 wherein the braze comprises a metal selected from the group consisting of Ag, Al, Au, Bi, Cd, Co, Cr, Cu, Fe, Ga, In, Mg, Mn, Ni, Pb, Sb, Sn, Pt, Pd, Tl, and Zn, and mixtures or combinations thereof; and wherein the first bottom bonding layer contains no more than three metals which exclude Co, Cr, and Ni.

9. A method of claim 4 wherein the ceramic is selected from the group consisting of alumina, boron carbide, boron nitride, diamond, boron carbide, silicon carbide, silicon nitride, titanium boride, titanium carbide, zirconia, zirconium carbide; and wherein the bonded ceramic structure is a ceramic cutting and abrading tool.

10. A method of claim 4 wherein the ceramic is diamond and the bonded ceramic structure is a diamond heat sink.

11. A method as in claim 10 wherein the substrate is selected from the group consisting of Ag, AlN, Au, C, BeO, Fe, graphite, Mo, Ni, Pt, Si, SiC, diamond, silicon nitride, Al, Co, Cr, Cu, Ir, Mn, Os, Rd, Rh, V, W, steel, alumina, boron carbide, boron nitride, silicon oxide, tungsten carbide, ceramic superconductors, thermally conductive composite, and a combination thereof;

wherein the ceramic supplying step comprises supplying a diamond body having a side surface, a top major surface, and a bottom major surface;

wherein the positioning step comprises positioning the diamond onto the substrate, with the at least a part of the first bottom major surface of the diamond in contact with the top surface of the substrate; and wherein the furnishing and heating steps comprise providing the first bottom bonding layer to consist mostly of a single braze metal selected from the group consisting of copper, silver, aluminum, and gold.

12. A method as in claim 11 wherein the furnishing and heating steps comprise providing on the diamond body the first bottom bonding layer having a thickness of no more than 5 mils.

13. A method as in claim 11 including the additional step of providing a side bonding layer on the side surface of the diamond body leaving no air gap or cracks therebetween for preventing the formation of thermally resistive or insulating wall therebetween.

14. A method as in claim 13 wherein the additional providing step comprises providing the side bonding layer to extend, by design, substantially above the top major surface of the diamond body so that the heat spreading outward from the diamond body has a significant component in a sideways upward direction.

15. A method as in claim 13 including supplying a similar, second diamond body also having a side surface, a top major surface, and a bottom major surface;

positioning the second diamond body adjacent to the first diamond body with at least a part of its bottom major surface in contact with the top surface of the substrate;

providing a similar, second bottom bonding layer to bond the at least a part of the bottom major surface of the second diamond body onto the same top surface of the substrate; and using the side bonding layer to bond together the oppositely facing side surfaces of the two adjacent diamond bodies for achieving lateral heat spreading from one of the two diamond bodies to the other.

16. A method as in claim 14 including terminating the top major surfaces of the two diamond bodies and the side bonding layer to have a common coplanar top surface for facilitating the mounting thereon of an electrical circuit chip;

the bottom area of the electrical circuit chip being greater than any one of the two top major surfaces on the diamond bodies.

17. A method as in claim 10 wherein the carbide-forming metal is selected from the group consisting of Si, Mo, W, and Fe.

18. A method as in claim 3 wherein the substrate consists essentially of the single metal element.

19. A method as in claim 1 wherein the carbide-forming metal and the substrate are of the same metal element selected from the group consisting of Mo, Si, Fe, and W.

20. A method as in claim 19 wherein the ceramic is selected from the group consisting of diamond, carbon, graphite, silicon carbide, silicon nitride, carbon composite, and graphite composite.

21. A method as in claim 1 wherein:

the selecting step comprises selecting the substrate from the group consisting of Ag, AlN, Au, C, BeO, Fe, graphite, Mo, Ni, Pt, Si, SiC, diamond, silicon nitride, Al, Co, Cr, Cu, V, W, steel, alumina, silicon carbide, ceramic superconductors, thermally conductive composite, and a combination thereof;

the supplying step comprises supplying a plurality of bodies of the ceramic selected from the group consisting of diamond and silicon carbide, each ceramic body having a side surface, a top major surface, and a bottom major surface;

the positioning step comprises positioning the plurality of the ceramic bodies adjacent to, and in contact relation with, each other or one another, onto a selected portion of a top surface of the substrate with the at least two bottom major surfaces of the ceramic bodies in contact with the selected portion of the top surface of the substrate; and the furnishing and heating steps comprise:

providing the first bottom bonding layer microscopically substantially perfectly bonding the at least two ceramic bodies onto the selected portion of the substrate; and providing the at least one side bonding layer microscopically substantially perfectly bonding the at least two contacting side major surfaces together;

the at least two top major surfaces and the at least one side bonding layer forming a common, coplanar top surface;

the at least one side bonding layer being sufficiently thin to form a monolayer of the ceramic bodies with their bonded bottom major surfaces covering substantially 100% of the selected portion of the top surface of the substrate thereby achieving efficient heat spreading from one of the ceramic bodies to the other ceramic body or bodies.

22. A method of making a bonded ceramic structure comprising a ceramic bonded onto a substrate, comprising:

supplying at least one body of the ceramic;

selecting the substrate to consist essentially of a single metal element selected from the group consisting of Au, B, Fe, Hf, Ir, La, Li, Mn, Mo, Os, Pd, Re, Rh, Ru, Si, Th, U, V, and W;

without applying external pressure during the entire bonding process the single metal element being capable of chemically reacting, above a first temperature, with the ceramic to produce between the ceramic and substrate, a void-free and microcrack-free interfacial bonding material of up to 0.125 mm thick and comprising essentially of the eutectic, the bonding material being capable of directly and chemically bonding, microscopically substantially perfectly, to both the ceramic and the substrate; and causing, at a second temperature sufficiently higher than the first temperature but without the external pressure, the chemical reaction between the ceramic and the single metal element substrate to take place in order to produce the eutectic interfacial bonding material which directly bonds on one side thereof to the ceramic and on another side thereof to the substrate thereby forming the bonded ceramic structure.

23. A method as in claim 22 wherein the selecting step comprises selecting the single metal element which is capable of forming, at the second temperature of less than 1350° C., a carbide with the ceramic, the eutectic comprising essentially of the thus formed carbide.

24. A method as in claim 22 wherein:

the supplying step comprises supplying the at least one ceramic body to have a bottom surface;

the selecting step comprises selecting the substrate to have a top surface; and the causing step comprises placing the bottom surface of the at least one ceramic body on the top surface of the substrate; and heating, without pressurizing, the ceramic and substrate to produce the interfacial bonding material in a layer form having a top major surface and a bottom major surface;

the interfacial bonding material layer directly bonding on the top major surface thereof to the bottom surface of the ceramic and on the bottom major surface thereof to the top surface of the substrate.

25. A method as in claim 22 wherein:

the selecting step comprises selecting as the substrate material a pure metal selected from the group consisting of molybdenum and silicon;

the supplying step comprises supplying diamond having the bottom surface at least 1.5 mm in one dimension and positioned in contact with the top surface of the molybdenum substrate; and the heating step comprises heating to a temperature of less than about 1,050° C. in a gaseous mixture of hydrogen and a gas selected from the group consisting of methane ($CH_4$) and propane.

26. A method as in claim 24 wherein the heating step comprises heating together the ceramic and the substrate in a gaseous environment comprising a gas selected from the group consisting of hydrogen, nitrogen, hydrocarbon gas, and mixtures thereof.

27. A method as in claim 26 wherein the the gaseous environment is selected from the group consisting of at least one hydrogen-containing gas, at least one carbon-containing gas, and a mixture thereof.

28. A method as in claim 23 wherein the interfacial bonding material consists essentially of the eutectic which comprises the chemically formed carbide.

29. A method as in claim 22 wherein the single metal element is selected from the group consisting of Mo, Si, Fe, and W.

30. A method as in claim 22 wherein the ceramic is selected from the group consisting of AlN, C, diamond, BeO, graphite, Si, SiC, silicon nitride, boron carbide, boron nitride, alumina, zirconia, titanium boride, titanium carbide, zirconium carbide, tungsten carbide, thermally conductive composite, and a combination thereof.

31. A method as in claim 22 wherein:

the selecting step comprises selecting the substrate from the group consisting of Ag, AlN, Au, C, BeO, Fe, graphite, Mo, Ni, Pt, Si, SiC, diamond, silicon nitride, Al, Co, Cr, Cu, V, W, steel, alumina, silicon carbide, ceramic superconductors, thermally conductive composite, and a combination thereof;

the supplying step comprises supplying a plurality of bodies of the ceramic selected from the group consisting of diamond and silicon carbide, each ceramic body having a side surface, a top major surface, and a bottom major surface;

the positioning step comprises positioning the plurality of the ceramic bodies adjacent to, and in contact relation with, each other or one another, onto a selected portion of a top surface of the substrate with the at least two bottom major surfaces of the ceramic bodies in contact with the selected portion of the top surface of the substrate; and the causing step comprise:

providing the first bottom bonding layer microscopically substantially perfectly bonding the at least two ceramic bodies onto the selected portion of the substrate; and providing the at least one side bonding layer microscopically substantially perfectly bonding the at least two contacting side major surfaces together;

the at least two top major surfaces and the at least one side bonding layer forming a common, coplanar top surface;

the at least one side bonding layer being sufficiently thin to form a monolayer of the ceramic bodies with their bonded bottom major surfaces covering substantially 100% of the selected portion of the top surface of the substrate thereby achieving efficient heat spreading from one of the ceramic bodies to the other ceramic body or bodies.

32. A method of making a diamond cutting and abrading tool comprising the steps of:
(A) mixing a carbide-forming substance containing at least one element capable of forming a carbide, a braze which alloys with the element and a temporary binder to provide a coating material;
the at least one carbide-forming element being selected from the group consisting of Au, B, Ir, La, Li, Mn, Mo, Os, Re, Rh, Ru, Si, Th, U, V, W, and mixtures or alloys thereof, in the form of either a pure metal or a chemical compound;
(B) applying the coating material and a layer of diamond particles to a tool substrate; and
(C) without applying external pressure during the entire bonding process, heating the product of step (B) at a temperature sufficient to initially form an element carbide coating in the form of a chemical bonding layer on the diamond and thereafter to braze the element carbide coated diamond to the tool substrate;
the chemical bonding layer being microscopically substantially perfect and containing no voids and microcracks.

33. The method of claim 32 wherein the applying step comprises applying at least a monolayer of the diamond particles thereover.

34. The method of claim 32 wherein the heating step comprises heating to a temperature of less than 1350° C. and without externally pressurizing the diamond particles against the tool substrate.

35. The method of claim 34 wherein the heating step comprises heating in a gaseous or non-vacuum atmosphere.

36. A method as in claim 35 wherein the carbide-forming substance consists essentially of a carbide-forming material selected from the group consisting of Au, B, Co, Cr, Fe, Ir, La, Li, Mn, Mo, Ni, Re, Rh, Ru, Si, Ta, Th, Ti, U, V, W, Zr, and mixtures or alloys thereof;
the carbide-forming material being in a form selected from the group consisting of pure metal or chemical compounds thereof.

37. A method as in claim 35 wherein the carbide-forming substance consists essentially of a single carbide-forming material selected from the group consisting of Au, B, Co, Cr, Fe, Ir, La, Li, Mn, Mo, Ni, Re, Rh, Ru, Si, Ta, Th, Ti, U, V, W, and Zr, in a form selected from the group consisting of a pure metal or a chemical compound thereof;
the applying step comprises applying to the tool substrate a layer of the coating material and the diamond particles;
the applied layer being substantially uniform in chemical composition in any plane contained therein which is parallel to the top surface of the tool substrate.

38. The method of claim 35 wherein the carbide-forming element is a carbide-forming metal selected from the group consisting of W, Mo, Fe, Mn, Si, and mixture of combination thereof, the carbide-forming metal being in a form selected from the group consisting of a pure metal and a chemical compound thereof.

39. A method as in claim 32 wherein the mixing step comprises controlling the sizes and gravitational segregation of the mixed powders in the temporary binder to achieve a substantially uniform composition of the element carbide coating at a specified distance from the surface of the substrate.

40. A method of making a bonded ceramic structure comprising a ceramic bonded onto a substrate, comprising:
selecting the substrate having a top surface;
supplying the ceramic having a bottom surface;
positioning the ceramic to have at least a part of its bottom surface in contact with the top surface of the substrate;
furnishing at the contact area between the ceramic and the substrate a bonding substance containing a material which chemically reacts above a first temperature with the ceramic to form a chemical composition capable of microscopically substantially perfectly chemically bonding to both the ceramic and the substrate;
heating the ceramic in contact with the substrate above the first temperature to cause the chemical reaction to occur thereby forming a bonding layer of the chemical composition which microscopically substantially perfectly bonds chemically the top surface of the substrate to the at least a part of the bottom surface of the ceramic; and
controlling the thickness of the bonding layer to an accuracy of less than 100 Angstroms.

41. A method as in claim 40 wherein the controlling step comprises controlling the thickness of the bonding layer to an accuracy of less than 10 Angstroms.

42. A method as in claim 40 including the additional step of:
providing in the bonding layer a stress-suppressing substance which divides the bonding layer into a plurality of bonding regions to thereby minimize the transmission of mismatch stress between the ceramic and substrate from one bonding region to another.

43. A method as in claim 40 wherein the bonding layer is either macroscopically or microscopically void-free and crack-free.

44. A method as in claim 40 wherein:
the heating step comprises heating, without pressurizing the ceramic, in a gaseous ambient selected from the group consisting essentially of at least one hydrogen-containing gas, at least one carbon-containing gas, and a mixture thereof;
the ceramic is diamond or silicon carbide;
both the substrate and the bonding substance consist essentially of a single metal selected from the group consisting of Fe, Si, Mo, and W; and
the first temperature is less than 1,350° C.

45. A method as in claim 22 wherein:
the selecting step comprises selecting as the substrate material a pure metal selected from the group consisting of molybdenum and silicon;
the supplying step comprises supplying diamond having the bottom surface at least 1.5 mm in one dimension thereof and positioned in contact with the top surface of the pure metal substrate; and
the heating step comprises heating to a temperature of less than about 1,050° C. in a flowing gaseous mixture of hydrogen and a gas selected from the group consisting of methane ($CH_4$) and propane.
heating together the ceramic and the substrate in a gaseous reducing environment containing a hydrocarbon gas.

46. A method as in claim 40 wherein the substrate is a material selected from the group consisting of a metal and a ceramic.

47. A method as in claim 40 wherein the ceramic is selected from the group consisting of diamond, carbon, graphite, silicon carbide, silicon nitride, ceramic superconductor, and composite containing one of more of these ceramics; and
wherein the substrate is selected from the group consisting of Ag, Al, Au, C, Co, Cr, Cu, Fe, Ir, Mn, Me, Ni, Os, Rd, Rh, Si, V, W, steel, graphite, diamond, alumina, aluminum nitride, boron carbide, boron nitrider, silicon carbide, silicon nitride, silicon oxide, tungsten carbide, and ceramic superconductor.

48. A method as in claim 40 wherein:
the selecting step comprises selecting molybdenum as the substrate material;
the supplying step comprises supplying diamond having the bottom surface at least 1.5 mm in one dimension and positioned in contact with the top surface of the molybdenum substrate; and
the heating step comprises heating to a temperature of less than 1,050° C. or 1,000° C. in a flowing hydrogen-methane (CH$_4$) mixture.

49. A method as in claim 40 wherein:
the selecting step comprises selecting the substrate from the group consisting of Ag, AlN, Au, C, BeO, Fe, graphite, Mo, Ni, Pt, Si, SiC, diamond, silicon nitride, Al, Co, Cr, Cu, V, W, steel, alumina, silicon carbide, ceramic superconductors, thermally conductive composite, and a combination thereof;
the supplying step comprises supplying a plurality of bodies of the ceramic selected from the group consisting of diamond and silicon carbide, each ceramic body having a side surface, a top major surface, and a bottom major surface;
the positioning step comprises positioning the plurality of the ceramic bodies adjacent to, and in contact relation with, each other or one another, onto a selected portion of the top surface of the substrate with the at least two bottom major surfaces of the ceramic bodies in contact with the selected portion of the top surface of the substrate; and
the furnishing and heating steps comprise:
providing the first bottom bonding layer microscopically substantially perfectly bonding the at least two ceramic bodies onto the selected portion of the substrate; and
providing the at least one side bonding layer microscopically substantially perfectly bonding the at least two contacting side major surfaces together;
the at least two top major surfaces and the at least one side bonding layer forming a common, coplanar top surface;
the at least one side bonding layer being sufficiently thin to form a monolayer of the ceramic bodies with their bonded bottom major surfaces covering substantially 100% of the selected portion of the top surface of the substrate thereby achieving efficient heat spreading from one of the ceramic bodies to the other ceramic body or bodies.

* * * * *